(12) United States Patent
Mizuguchi et al.

(10) Patent No.: US 9,393,020 B2
(45) Date of Patent: Jul. 19, 2016

(54) LIGATOR AND LIGATION METHOD

(75) Inventors: Toru Mizuguchi, Hokkaido (JP); Koichi Hirata, Hokkaido (JP); Masaki Kawamoto, Hokkaido (JP); Makoto Meguro, Hokkaido (JP)

(73) Assignee: Sapporo Medical University, Sapporo-shi, Hokkaido (JP)

( * ) Notice: Subject to any disclaimer, the term of this patent is extended or adjusted under 35 U.S.C. 154(b) by 452 days.

(21) Appl. No.: 13/878,502

(22) PCT Filed: Oct. 5, 2011

(86) PCT No.: PCT/JP2011/072942
§ 371 (c)(1),
(2), (4) Date: Jun. 12, 2013

(87) PCT Pub. No.: WO2012/046757
PCT Pub. Date: Apr. 12, 2012

(65) Prior Publication Data
US 2013/0267965 A1    Oct. 10, 2013

(30) Foreign Application Priority Data
Oct. 5, 2010   (JP) ................................. 2010-226110

(51) Int. Cl.
*A61B 17/10*   (2006.01)
*A61B 17/12*   (2006.01)
*A61B 17/00*   (2006.01)

(52) U.S. Cl.
CPC . *A61B 17/12013* (2013.01); *A61B 2017/00349* (2013.01)

(58) Field of Classification Search
USPC ................... 606/139, 144–148; 248/301, 304
See application file for complete search history.

(56) References Cited

U.S. PATENT DOCUMENTS

| 2,143,910 | A | * | 1/1939 | Didusch | 606/151 |
| 3,665,926 | A | * | 5/1972 | Flores | 606/139 |
| 3,762,418 | A | * | 10/1973 | Wasson | 606/226 |

(Continued)

FOREIGN PATENT DOCUMENTS

| JP | 06-233774 A | 8/1994 |
| JP | 2002-095667 A | 4/2002 |

(Continued)

OTHER PUBLICATIONS

International Search Report of the International Searching Authority mailed Nov. 1, 2011 for the corresponding international application No. PCT/JP2011/072942 (with English translation).

*Primary Examiner* — Tuan V Nguyen
(74) *Attorney, Agent, or Firm* — Muncy, Geissler, Olds & Lowe, P.C.

(57) ABSTRACT

A ligator for ligating body duct(s), said ligator enabling quick, easy and damage-free repetition of ligation and release of one or more body ducts in a body cavity through an operation outside the body cavity, and having an excellent performance of blocking the flow of a body fluid such as blood or lymph in a body duct. In an abdominal surgery, the ligator can be provided at such a position as not disturbing the surgery per se or hindering the vision during the surgery, while leaving the back-end thereof outside the body cavity, and can be operated outside the body cavity. In an endoscopic surgery, the ligator can be inserted from an opening that is a surgical wound while leaving the back-end thereof outside the body cavity, and can be operated outside the body cavity.

15 Claims, 8 Drawing Sheets

(56) References Cited

U.S. PATENT DOCUMENTS

| | | | |
|---|---|---|---|
| 3,877,434 A * | 4/1975 | Ferguson et al. | 606/158 |
| 5,318,575 A * | 6/1994 | Chesterfield et al. | 606/151 |
| 5,340,360 A * | 8/1994 | Stefanchik | A61B 17/1285 227/901 |
| 8,579,901 B1 * | 11/2013 | Foerster | A61B 17/82 606/74 |
| 2001/0041901 A1 | 11/2001 | Furusawa | |
| 2004/0116943 A1 * | 6/2004 | Brandt et al. | 606/144 |
| 2005/0125036 A1 * | 6/2005 | Roby | 606/228 |
| 2005/0209609 A1 * | 9/2005 | Wallace | A61B 17/221 606/113 |
| 2007/0225763 A1 * | 9/2007 | Zwolinski et al. | 606/228 |
| 2012/0232589 A1 * | 9/2012 | Fedinec | A61B 17/06166 606/228 |

FOREIGN PATENT DOCUMENTS

| | | |
|---|---|---|
| JP | 2004-305273 A | 11/2004 |
| JP | 2007-296373 A | 11/2007 |
| JP | 2008-049198 A | 3/2008 |
| JP | 2008-264106 A | 11/2008 |

* cited by examiner

Tumor

Region Where Tumor
Is Excised

Region Where Tumor
Is Excised

LIGATOR AND LIGATION METHOD

CROSS REFERENCE TO RELATED APPLICATIONS

This application is a U.S. national stage application of PCT/JP2011/072942 filed on Oct. 5, 2011, and claims priority to, and incorporates by reference, Japanese Patent Application No. 2010-226110 filed on Oct. 5, 2010.

TECHNICAL FIELD

The present invention relates to a ligator and a ligation method and, more particularly, to a ligator for ligating one or two or more body ducts in a body cavity, the ligator including a predetermined tubular member and a predetermined string member, a method of ligating the body ducts, and a method of ligating flexible ducts that are present on the inside of a closed spatial body and through which fluid circulates.

BACKGROUND ART

Temporary ligation of body ducts such as blood vessels is performed in ablative surgery of a disease region, plastic surgery such as a change of a duct line, and the like. Various instruments for performing ligating operation have been developed. For example, as an instrument used for temporary ligation of body ducts in abdominal surgery, there are known, for example, a blood vessel forceps for nipping and ligating body ducts and a tape for ligation looped double around body ducts and drawn to ligate the body ducts. Patent Literature 1 discloses a tissue ligator for nipping and ligating body ducts. On the other hand, as an instrument used for ligation of body ducts in laparoscopic surgery, there are known, for example, clips made of resin and made of metal. Patent Literature 2 discloses a clip device for a living tissue for drawing out an operation wire and continuously performing ligation by a clip.

CITATION LIST

Patent Literature

Patent Literature 1: Japanese Patent Application Laid-Open Publication No. 6-233774
Patent Literature 2: Japanese Patent Application Laid-Open Publication No. 2008-49198

SUMMARY OF INVENTION

Technical Problem

However, in the abdominal surgery, the blood vessel forceps or the tissue ligator disclosed in Patent Literature 1 is detained in a range from a ligating region to the vicinity of the ligating region to perform the surgery. Therefore, it is likely that the blood vessel forceps or the tissue ligator disturbs the surgery and hinders the vision in the surgery. On the other hand, in the laparoscopic surgery, an instrument has to enable a surgeon to insert the instrument from an opening, which is a surgical wound, and ligate body ducts while operating the instrument on the outside of a body cavity. It is difficult to use the blood vessel forceps or the tissue ligator disclosed in Patent Literature 1 for the purpose of ligating body ducts in the laparoscopic surgery. Further, both of the clips made of resin and made of metal and the clip device disclosed in Patent Literature 2 require specific work for removing the clip. Therefore, the clips and the clip device are poor in quickness and convenience.

The present invention has been devised to solve the problems and it is an object of the present invention to provide a ligator for ligating body ducts, the ligator enabling quick, easy and damage-free repetition of ligation and release of one or more body ducts in a body cavity through an operation outside the body cavity, and having an excellent performance of blocking the flow of a body fluid such as blood or lymph in a body duct, in abdominal surgery, the ligator being able to be provided at such a position as not disturbing the surgery per se or hindering the vision during the surgery, while leaving the back-end thereof outside the body cavity, and in laparoscopic surgery, the ligator being able to be inserted from an opening that is a surgical wound, while leaving the back-end thereof outside the body cavity, and to be operated outside the body cavity, a method for ligating body ducts, the method being effective for blocking the flow of a body fluid such as blood or lymph in a body duct and being able to be operated outside a body cavity and therefore enabling quick, easy and damage-free repetition of ligation and release of the body ducts, and a method of ligating flexible ducts that are present on the inside of a closed spatial body and through which fluid circulates, the method being effective for blocking the flow of the fluid in the flexible ducts that are present on the inside of the closed spatial body and through which the fluid circulates and being able to be operated on the outside of the closed spatial body and therefore enabling quick and easy repetition of ligation and release of the flexible ducts.

Solution to Problem

The inventors have found as a result of the earnest researches that it is possible to ligate a body duct quickly, easily, and without causing damage by leading out, from a back-end portion of a tubular member, a front-end portion and a back-end portion of a string member looped around a ligation planned region of the body duct in a body cavity and drawing the front-end portion and the back-end portion of the string member on the outside of the body cavity or pushing the tubular member in a front-end direction thereof. Further, the inventors have found that such a ligation method can be applied to ligation of a flexible duct that is present on the inside in a closed spatial body and through which fluid circulates. Consequently, the inventors have completed inventions explained below.

(1) A ligator for ligating one or more body ducts in a body cavity, the ligator including a tubular member and a string member for bringing the body ducts close to a front-end portion of the tubular member, wherein the tubular member allows at least a pair of the string members to be inserted therethrough and has length extending from a ligating position of the body ducts in the body cavity to the outside of the body cavity, and the string member has length equal to or larger than a double of the length extending from the ligating position to the outside of the body cavity.

(2) The ligator described in (1), wherein the string member has a shape and size for preventing a contact section that comes into contact with the body ducts from causing damage to the body ducts when the body ducts are brought close to the front-end portion of the tubular member and ligated.

(3) The ligator described in (2), wherein the contact section of the string member is belt-like and has width larger than 3 millimeters.

(4) The ligator described in any one of (1) to (3), wherein the string member has scales marked in positions before and behind a portion where the string member is looped around the body ducts and led out from a back-end portion of the tubular member.
(5) The ligator described in any one of (1) to (4), wherein the tubular member is a tubular member that is not bent by a pressing force received in a longitudinal direction thereof or is not reduced in length in the longitudinal direction.
(6) The ligator described in any one of (1) to (5), wherein the tubular member has marked thereon a scale indicating distances from a front-end and/or a back-end thereof.
(7) The ligator described in any one of (1) to (6), wherein the tubular member is chamfered at end edges of a front-end and/or a back-end thereof.
(8) The ligator described in any one of (1) to (7), further comprising a holding instrument that can hold an end portion of the string member while being inserted through the tubular member, through which the string member is inserted.
(9) The ligator described in (8), wherein the holding instrument includes, at a front-end portion thereof, a hook-like section formed in a hook shape capable of catching a singularity of or a pair of the string members and drawing the string members into the tubular member.
(10) A method of ligating a body duct in laparoscopic surgery, the method including: a string member front-end portion arranging step for inserting a front-end portion of a tubular member, through which a string member is inserted, into a body cavity from a first insertion hole and arranging, in the vicinity of a ligation planned region of the body duct, a front-end portion of the string member led out from the front-end portion of the tubular member while leaving a back-end portion thereof outside the body cavity; a string member looping-around step for inserting a first holding instrument into the body cavity from a second insertion hole, holding the front-end portion of the string member, and looping the string member around the ligation planned region of the body duct; a second holding instrument inserting-through step for inserting a second holding instrument from the back-end portion of the tubular member, through which the string member is inserted, and leading out the second holding instrument from the front-end portion of the tubular member; a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and a ligating step for ligating the body duct by drawing the drawn-out front-end portion and the back-end portion of the string member and/or pushing the tubular member in a front-end direction thereof.
(11) A method of ligating a body duct in laparoscopic surgery, the method including: a string member front-end portion arranging step for holding a front-end portion of a string member with a first holding instrument, inserting the front-end portion of the string member into a body cavity from a first insertion hole, and arranging, in the vicinity of a ligation planned region of the body duct, the front-end portion of the string member while leaving a back-end portion thereof outside the body cavity; a string member looping-around step for inserting a second holding instrument into the body cavity from a second insertion hole, holding the front-end portion of the string member, and looping the string member around the ligation planned region of the body duct; a string member front-end portion drawing-out step for holding the front-end portion of the looped-around string member with the first holding instrument and drawing out the front-end portion of the string member to the outside of the body cavity from the first insertion hole; a tubular member arranging step for inserting, from a front-end portion of a tubular member, both end portions of the string member drawn out to the outside of the body cavity from the first insertion hole, leading out both ends of the string member from a back-end portion of the tubular member, inserting the front-end portion of the tubular member into the body cavity from the first insertion hole, and arranging the front-end portion of the tubular member in the vicinity of the ligation planned region of the body duct while leaving the back-end portion thereof outside the body cavity; and a ligating step for ligating the body duct by drawing both ends of the string member led out from the back-end portion of the tubular member and/or pushing the tubular member in a front-end direction thereof.
(12) A method of ligating a body duct in laparoscopic surgery, the method including: a string member front-end portion arranging step for holding a front-end portion of a string member with a first instrument, inserting the front-end portion of the string member into a body cavity from a first insertion hole, and arranging the front-end portion of the string member in the vicinity of a ligation planned region of the body duct while leaving a back-end portion thereof outside of the body cavity; a string member looping-around step for inserting a front-end portion of a tubular member, through which a second holding instrument is inserted, into the body cavity from a second insertion hole, holding the front-end portion of the string member with the second holding instrument led out from the front-end of the tubular member while leaving a back-end portion thereof outside the body cavity, and looping the string member around the ligation planned region of the body duct; a string member front-end portion drawing-out step for drawing the front-end portion of the looped-around string member into the tubular member while keeping the front-end portion held by the second holding instrument, drawing out the front-end portion of the string member from the back-end portion of the tubular member, and drawing the back-end portion of the string member into the body cavity from the first insertion hole; a third holding instrument inserting-through step for inserting a third holding instrument from the back-end portion of the tubular member and leading out the third holding instrument from the front-end portion of the tubular member; a string member back-end portion drawing-out step for holding the back-end portion of the string member with the third holding instrument, drawing the back-end portion of the string member into the tubular member, and drawing out the back-end portion of the string member from the back-end portion of the tubular member; and a ligating step for ligating the body duct by drawing the drawn-out front-end portion and the back-end portion of the string member and/or pushing the tubular member in a front-end direction thereof.
(13) A method of ligating a body duct in laparoscopic surgery, the method including: a string member front-end portion arranging step for holding a front-end portion of a tubular member with a first holding instrument, inserting the front-end portion of the string member into a body cavity from a first insertion hole, and arranging, in the vicinity of a ligation planned region of the body duct, the front-end portion of the string member while leaving a back-end portion thereof outside the body cavity; a string member looping-around step for inserting a second holding instrument into the body cavity from a second insertion hole, holding the front-end portion of the string member, and looping the string member around the ligation planned region of the body duct; a string member front-end portion drawing-out step for drawing out the front-end portion of the looped-around string member from the second insertion hole while keeping the front-end portion of the looped-around string member held by the second holding instrument, drawing the back-end portion of the string member into the body cavity from the first insertion hole; a string member back-end portion drawing-out step for inserting a third holding instrument into the body cavity from the second insertion hole, holding the back-end portion of the string member, and drawing out the back-end portion of the string member from the second insertion hole; a tubular member arranging step for inserting, from the front-end portion of the tubular member, the drawn-out front-end portion and the back-end portion of the string member, leading out the front-end portion and the back-end portion of the string member from the back-end portion of the tubular member, inserting the front-end portion of the tubular member into the body cavity from the second insertion hole, and arranging the front-end portion of the tubular member in the vicinity of the ligation planned region of the body duct while leaving the back-end portion thereof outside the body cavity; and a ligating step for ligating the body duct by drawing the drawn-out front-end portion and the back-end portion of the string member from the back-end portion of the tubular member and/or pushing the tubular member in a front-end direction thereof.

(14) A method of ligating a body duct, the method including: a string member front-end portion arranging step for arranging a front-end portion of a tubular member, through which a string member is inserted, in the vicinity of a ligation planned region of the body duct while leaving a back-end portion thereof outside a body cavity to thereby arrange, in the vicinity of the ligation planned region of the body duct, a front-end portion of the string member led out from the front-end portion of the tubular member; a string member looping-around step for holding the front-end portion of the string member with a first holding instrument and looping the string member around the ligation planned region of the body duct; a second holding instrument inserting-through step for inserting a second holding instrument from the back-end portion of the tubular member, through which the string member is inserted, and leading out the second holding instrument from the front-end portion of the tubular member; a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and a ligating step for ligating the body duct by drawing the drawn-out front-end portion and the back-end portion of the string member and/or pushing the tubular member in a front-end direction thereof.

(15) The method described in any one of (10) to (14), wherein the string member has a shape and size for preventing a contact section that comes into contact with the body duct from causing damage to the body duct when the body duct is ligated.

(16) The method described in (15), wherein the contact section of the string member is belt-like and has width larger than 3 millimeters.

(17) The method described in any one of (10) to (16), wherein the string member has scales marked in positions before and behind a portion where the string member is looped around the body duct and led out from the back-end portion of the tubular member.

(18) The method described in any one of (10) to (17), wherein the tubular member is a tubular member that is not bent by a pressing force received in a longitudinal direction thereof or is not reduced in length in the longitudinal direction.

(19) The method described in any one of (10) to (18), wherein the tubular member has marked thereon a scale indicating distances from a front-end and/or a back-end thereof.

(20) The method described in any one of (10) to (19), wherein the tubular member is chamfered at an end edge of a front-end and/or a back-end thereof.

(21) A method of ligating a flexible duct that is present on the inside of a closed spatial body and through which fluid circulates, the method including: an insertion hole forming step for forming a first insertion hole communicating with the inside of the closed spatial body and a second insertion hole communicating with the inside of the closed spatial body; a string member front-end portion arranging step for inserting a front-end portion of a tubular member, through which a string member is inserted, into the closed spatial body from the first insertion hole and arranging, in the vicinity of a ligation planned region of the flexible duct, through which the fluid circulates, a front-end portion of the string member led out from the front-end portion of the tubular member while leaving a back-end portion thereof outside the closed spatial body; a string member looping-around step for inserting a first holding instrument into the closed spatial body from the second insertion hole, holding the front-end portion of the string member, and looping the string member around the ligation planned region of the flexible duct, through which the fluid circulates; a second holding instrument inserting-through step for inserting a second holding instrument from the back-end portion of the tubular member, through which the string member is inserted, and leading out the second holding instrument from the front-end portion of the tubular member; a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and a ligating step for ligating the flexible duct, through which the fluid circulates, by drawing the drawn-out front-end portion and the back-end portion of the string member and/or pushing the tubular member in a front-end direction thereof.

(22) A method of ligating a flexible duct that is present on the inside of a closed spatial body and through which fluid circulates, the method including: an insertion hole forming step for forming a first insertion hole communicating with the inside of a closed spatial body and a second insertion hole communicating with the inside of the closed spatial body; a string member front-end portion arranging step for holding a front-end portion of a string member with a first holding instrument, inserting the front-end portion of the string member into the closed spatial body from the first insertion hole, and arranging, the front-end portion of the string member in the vicinity of a ligation planned region of the flexible duct, through which the fluid circulates, while leaving a back-end portion thereof outside the closed spatial body; a string member looping-around step for inserting a second holding instrument into the closed spatial body from the second insertion hole, holding the front-end portion of the string member, and looping the string member around the ligation planned region of the flexible duct, through which the fluid circulates; a string member front-end portion drawing-out step for holding the front-end portion of the looped-around string member with the first holding instrument and drawing out the front-end portion of the string member to the outside of the closed spatial body from the first insertion hole; a tubular member arranging step for inserting, from a front-end portion of a tubular member, both end portions of the string member drawn out to the outside of the closed spatial body from the first insertion hole, leading out both ends of the string member from a back-end portion of the tubular member, inserting the front-end portion of the tubular member into the closed spatial body from the first insertion hole, and arranging the front-end portion of the tubular member in the vicinity of the ligation planned region of the flexible duct, through which the fluid circulates, while leaving the back-end portion thereof outside the closed spatial body; and a ligating step for ligating the flexible duct, through which the fluid circulates, by drawing both ends of the string member led out from the back-end portion of the tubular member and/or pushing the tubular member in a front-end direction thereof.

(23) A method of ligating a flexible duct that is present on the inside of a closed spatial body and through which fluid circulates, the method including: an insertion hole forming step for forming a first insertion hole communicating with the inside of the closed spatial body and a second insertion hole communicating with the inside of the closed spatial body; a string member front-end portion arranging step for holding a front-end portion of a string member with a first holding instrument, inserting the front-end portion of the string member into the closed spatial body from the first insertion hole, and arranging the front-end portion of the string member in the vicinity of a ligation planned region of the flexible duct, through which the fluid circulates, while leaving a back-end portion thereof outside of the closed spatial body; a string member looping-around step for inserting a front-end portion of a tubular member, through which a second holding instrument is inserted, into the closed spatial body from the second insertion hole, holding the front-end portion of the string member with the second holding instrument led out from the front-end of the tubular member while leaving a back-end portion thereof outside the closed spatial body, and looping the string member around the ligation planned region of the flexible duct, through which the fluid circulates; a string member front-end portion drawing-out step for drawing the front-end portion of the looped-around string member into the tubular member while keeping the front-end portion held by the second holding instrument, drawing out the front-end portion of the string member from the back-end portion of the tubular member, and drawing the back-end portion of the string member into the closed spatial body from the first insertion hole; a third holding instrument inserting-through step for inserting a third holding instrument from the back-end portion of the tubular member and leading out the third holding instrument from the front-end portion of the tubular member; a string member back-end portion drawing-out step for holding the back-end portion of the string member with the third holding instrument, drawing the back-end portion of the string member into the tubular member, and drawing out the back-end portion of the string member from the back-end portion of the tubular member; and a ligating step for ligating the flexible duct, through which the fluid circulates, by drawing the drawn-out front-end portion and the back-end portion of the string member and/or pushing the tubular member in a front-end direction thereof.

(24) A method of ligating a flexible duct that is present on the inside of a closed spatial body and through which fluid circulates, the method including: an insertion hole forming step for forming a first insertion hole communicating with the inside of the closed spatial body and a second insertion hole communicating with the inside of the closed spatial body; a string member front-end portion arranging step for holding a front-end portion of a string member with a first holding instrument, inserting the front-end portion of the string member into the closed spatial body from the first insertion hole, and arranging the front-end portion of the string member in the vicinity of a ligation planned region of the flexible duct, through which the fluid circulates, while leaving a back-end portion thereof outside the closed spatial body; a string member looping-around step for inserting a second holding instrument into the closed spatial body from the second insertion hole, holding the front-end portion of the string member, and looping the string member around the ligation planned region of the flexible duct, through which the fluid circulates; a string member front-end portion drawing-out step for drawing out the front-end portion of the looped-around string member from the second insertion hole while keeping the front-end portion of the looped-around string member held by the second holding instrument, drawing the back-end portion of the string member into the closed spatial body from the first insertion hole; a string member back-end portion drawing-out step for inserting a third holding instrument into the closed spatial body from the second insertion hole, holding the back-end portion of the string member, and drawing out the back-end portion of the string member from the second insertion hole; a tubular member arranging step for inserting, from the front-end portion of the tubular member, the drawn-out front-end portion and the back-end portion of the string member, leading out the front-end portion and the back-end portion of the string member from the back-end portion of the tubular member, inserting the front-end portion of the tubular member into the closed spatial body from the second insertion hole, and arranging the front-end portion of the tubular member in the vicinity of the ligation planned region of the flexible duct, through which the fluid circulates, while leaving the back-end portion thereof outside the body cavity; and a ligating step for ligating the flexible duct, through which the fluid circulates, by drawing the drawn-out front-end portion and the back-end portion of the string member and/or pushing the tubular member in a front-end direction thereof.

(25) A method of ligating a flexible duct that is present on the inside of a closed spatial body and through which fluid circulates, the method including: an opening step for opening the inside of the closed spatial body; a string member front-end portion arranging step for arranging a front-end portion of a tubular member, through which a string member is inserted, in the vicinity of a ligation planned region of the flexible duct, through which the fluid circulates, while leaving a back-end portion thereof outside the closed spatial body to thereby arrange, in the vicinity of the ligation planned region of the flexible duct, through which the fluid in the closed spatial body circulates, a front-end portion of the string member led out from the front-end portion of the tubular member; a string member looping-around step for holding the front-end portion of the string member with a first holding instrument and looping the string member around the ligation planned region of the flexible duct, through which the fluid circulates; a second holding instrument inserting-through step for inserting a second holding instrument from the back-end portion of the tubular member, through which the string member is inserted, and leading out the second holding instrument from the front-end portion of the tubular member; a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and a ligating step for ligating the flexible duct, through which the fluid circulates, by drawing the drawn-out front-end portion and the back-end portion of the string member and/or pushing the tubular member in a front-end direction thereof on the outside of the closed spatial body.

(26) The method described in any one of (21) to (25), wherein the tubular member is a tubular member that is not bent by a pressing force received in a longitudinal direction thereof or is not reduced in length in the longitudinal direction.

Advantageous Effects of Invention

With the ligator according to the present invention, the ligator enables quick, easy and damage-free repetition of ligation and release of one or two or more body ducts in a body cavity through an operation outside a body cavity. The ligator is excellent in blocking the flow of a body fluid such as blood or lymph in a body duct. In abdominal surgery, the ligator can be provided at such a position as not disturbing the surgery per se or hindering the vision during the surgery, while leaving the back-end thereof outside the body cavity. In laparoscopic surgery, the ligator can be inserted from an opening that is a surgical wound, while leaving the back-end thereof outside the body cavity, and can be operated outside the body cavity. With the method of ligating a body duct according to the present invention, the method is effective for blocking the flow of a body fluid such as blood or lymph in the body duct and can be operated outside a body cavity and therefore enables quick, easy and damage-free repetition of ligation and release of the body duct. For example, in laparoscopic liver resection, it is possible to surely excise a tumor in a deep part of the liver, which cannot be excised in the past, with an ordinary laparoscopic surgery skill without causing bleeding. Further, with the method of ligating a flexible duct that is present on the inside of a closed spatial body and through which fluid circulates according to the present invention, for example, even on the inside of the closed spatial body in which manual work is difficult, the method enables quick, easy and damage-free repetition of ligation and release of the flexible duct through operation on the outside of the closed spatial body.

DESCRIPTION OF EMBODIMENTS

Figure 1:
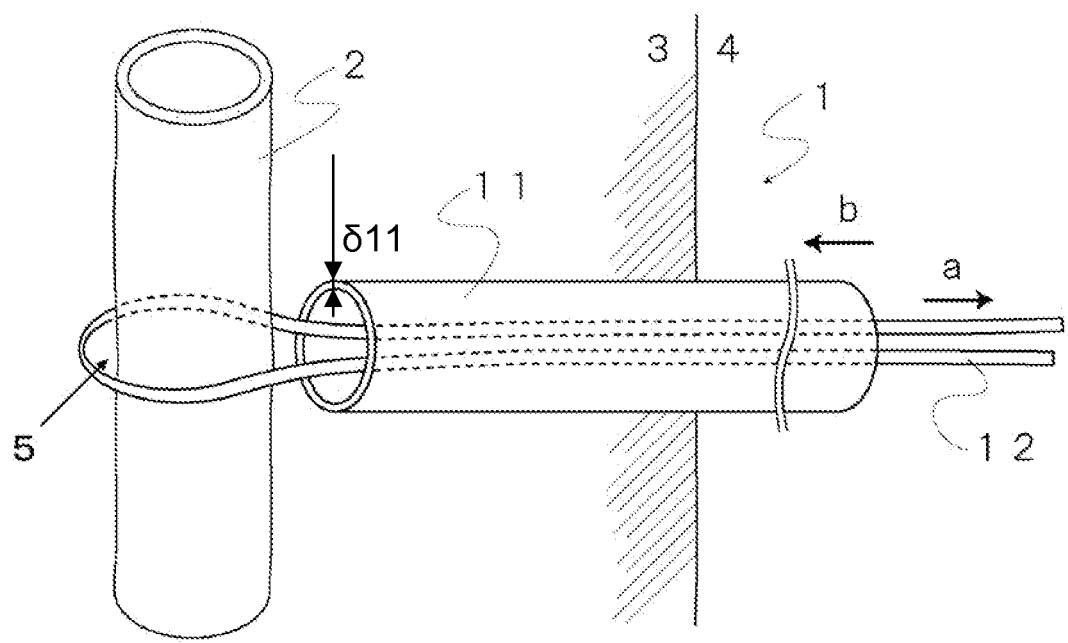
FIG. 1 is a diagram showing a first mode of a ligator according to the present invention.

A ligator and a ligation method according to the present invention are explained below in detail. The ligator according to the present invention is a ligator for ligating one or two or more body ducts in a body cavity. The ligator includes a tubular member through which at least two string members can be inserted and a string member for bringing the body ducts close to a front-end portion of the tubular member. The tubular member has length extending from a ligating position of the body ducts in the body cavity to the outside of the body cavity. The string member has length equal to or larger than a double of the length extending from the ligating position to the outside of the body cavity.

In the present invention, a "body cavity" refers to a cavity place in a body of an animal. Examples of the "body cavity" include an abdominal cavity and a thoracic cavity. A "body duct" refers to an organ having a tubular form in a living organism. Examples of the "body duct" include blood vessels such as an artery, a vein, and a portal vein, digestive organs such as an esophagus, a duodenum, a small intestine, and a large intestine, a lymph duct, a bile duct, a trachea, a urinary duct, a urethra, an oviduct, and a spermatic duct.

In the present invention, a "closed spatial body" is an object, a region, or the like having a space closed by a partition, a barrier, or the like. The inside and the outside of the space only have to be distinguished even after the closed space is opened. Examples of the "closed spatial body" include an object from which a closed space can be perceived such as a manhole besides objects having completely closed spaces such as a tank and a container. However, the "closed spatial body" is not limited to these objects. A "flexible duct" only has to be a duct having flexibility through which fluid can circulate. Examples of the "flexible duct" include a cross-linked polyethylene duct, a polybutene duct, and a rubber duct. However, the "flexible duct" is not limited to these ducts.

In the present invention, a "ligation" refers to narrowing or eliminating an air gap of an inner cavity of the body duct or the flexible duct in a specific position and stopping, suppressing, or blocking the flow of the circulating body fluid or fluid.

In the present invention, when the body duct is ligated, not only one body duct but also two or more body ducts can be ligated collectively. A body duct surrounded by a soft tissue can be ligated together with the tissue. For example, an artery, a vein, a portal vein, a bile duct, and the like surrounded by ligaments such as a hepatoduodenal ligament, a hepatogastric ligament, a gastrocolic ligament, and a mesentery can be ligated together with the ligaments.

In the present invention, "bringing a body duct close to a front-end portion of a tubular member" includes not only reducing the distance between the body duct and the front-end portion of the tubular member but also, for example, bringing the body duct and the front-end portion of the tubular member into contact with each other and drawing the body duct into the inside of the tubular member.

In the present invention, a "front-end portion of a tubular member", a "front-end portion of a string member", or a "front-end portion of a holding instrument" refers to an arbitrary portion from a front-end to the middle in a longitudinal direction of the tubular member, the string member, or the holding instrument. Similarly, a "back-end portion of a tubular member", a "back-end portion of a string member", or a "back-end portion of a holding instrument" refers to an arbitrary portion from a back-end to the middle in the longitudinal direction of the tubular member, the string member, or the holding instrument. An "end portion of a tubular member", an "end portion of a string member", or an "end portion of a holding instrument" refers to a front-end portion or a back-end portion of the tubular member, the string member, or the holding instrument.

In the present invention, a "tubular member" only has to have an inner diameter through which at least two string members can be inserted and desirably has an inner diameter through which two string members having width larger than 3 mm can be inserted. The outer diameter of the "tubular member" can be set as appropriate according to an environment in which the tubular member is used, operability of the tubular member, and the like.

In the present invention, the length of the tubular member only has to be length extending from a ligating position of the body duct in the body cavity to the outside of the body cavity or length extending from a ligating position of the flexible duct in the closed spatial body to the outside of the closed spatial body. The length of the tubular member can be set as appropriate according to the length of the string member in use, the shape and the material of the tubular member, the ligating position, a the position and the diameter of a surgical wound or an opening formed in the closed spatial body, the physique of a patient or the size and the scale of the closed spatial body, or the like. For example, in a ligator for ligating body ducts, the length of the tubular member can be set to 25 to 60 cm for adult male, 20 to 55 cm for adult female, 15 to 50 cm for infant, and the like. The tubular member may be a tubular member that can be cut to enable the length of the tubular member to be adjusted according to a situation.

In the present invention, as the shape of the tubular member and the shape of the cross section substantially perpendicular to the longitudinal direction of the tubular member, an arbitrary shape can be selected in a range in which the characteristics of the present invention are not spoiled. Examples of the shape of the tubular member include a columnar shape, a prism shape, a substantially conical shape, a substantially pyramid shape, an entasis shape, a lens shape, a drum shape, and a gourd shape. Examples of the shape of the cross section include a circular shape, an elliptical shape, an eyeglass shape (including two hollows), and a gourd shape. That is, the shape of the tubular member and the shape of the cross section substantially perpendicular to the longitudinal direction of the tubular member may be the same throughout the entire tubular member or may be different. As the front-end or the back-end of the tubular member, a shape not edged at the ends is desirable. For example, a chamfered shape is desirable.

The material of the tubular member that can be used in the present invention is not specifically limited in a range in which the characteristics of the present invention are not spoiled. Examples of the material include rubber such as natural rubber, synthetic rubber, and hard rubber, synthetic resin such as nylon elastomer, tetrafluoroethylene-perfluoro-alkoxyethylene copolymer resin (PFA), tetrafluoroethylene-hexafluoropropylene copolymer resin (FEP), polyvinylidene fluoride (PVDF), silicone, polyvinyl chloride, low density polyethylene (LDPE), high density polyethylene (HDPE), polyurethane, polypropylene, nylon, and polycarbonate, other natural resin, glass, and various kinds of metal. The material is not limited to a single material and may include two or more materials.

In the present invention, the tubular member is desirably a tubular member that is not bent by a pressing force received in the longitudinal direction or not reduced in length in the longitudinal direction. Such a tubular member can be formed by setting the inner diameter and the outer diameter, the length, the material, the structure, and the like of the tubular member as appropriate. The tubular member can be formed by, for example, using a hard material such as melamine resin, acrylic resin, urea resin, or hard rubber or, even if a soft material is used, incorporating a hard material such as a wire therein as a framework.

The color tone and the transparency of the tubular member can be selected as appropriate. For example, the tubular member can be formed to have high transparency to enable a user to visually check a state of the string member inserted through the tubular member, a ligated state of the body duct, and the like. Besides, the tubular member can be formed to assume a color different from the color of the inserted string member, the body duct, or the flexible duct.

In the present invention, a scale indicating a distance from the front-end or the back-end can be marked in the tubular member in a range in which the body cavity, the closed spatial body, the body duct, and the flexible duct are not adversely affected. A method of marking the scale is not specifically limited. Examples of the method include, besides a method of marking the scale using ink, in particular, ink having biocompatibility, a method of marking the scale by shaving the surface of a side surface of the tubular member and a method of marking the scale by applying embossing to the surface. The scale may be marked only in a part of the tubular member, for example, only a portion arranged on the outside of the body cavity or the outside of the closed spatial body when the body duct or the flexible duct is ligated or may be marked over the entire length of the tubular member as long as the scale can indicate the distance from the front-end or the back-end. A mode of the scale is not limited as long as the scale can indicates the distance from the front-end or the back-end. Examples of the scale include, besides a simple mark, for example, a scale formed by arranging symbols such as stripes or lines, bars, circles, triangles, diamonds, or the like at an appropriate interval, a scale formed by arranging numbers indicating distances at an appropriate interval, and a scale formed by arranging combinations of symbols and numbers at an appropriate interval.

The tubular member that can be used in the present invention may include any structure in a range in which the characteristics of the present invention are not spoiled. For example, the tubular member in the ligator according to the present invention may include a coating structure or a front-end portion structure formed by a soft material or a non-adhesive material, an air valve for gas leak prevention, or a clip for holding the string member.

In the present invention, a "string member" can be selected as appropriate in a range in which the characteristics of the present invention are not spoiled. Examples of the string member include a string-like member, a thread-like member, a belt-like member, and a tape-like member. However, the tape-like member is desirable. The length of the string member may be length equal to or larger than a double of length extending from the ligating position of the body duct in the body cavity to the outside of the body cavity or length equal to or larger than a double of length extending from the ligating position of the flexible duct in the closed spatial body to the outside of the closed spatial body. The length of the string member can be set as appropriate according to the length of the tubular member in use, the shape of the string member, the ligating position, the position and the diameter of a surgical wound or an opening formed in the closed spatial body, the physique of a patient or the size and the scale of the closed spatial body, or the like. For example, when the tubular member used simultaneously with the string member is 30 cm, the length of the string member can be set to 1 m and when the tubular member is 40 cm, the length of the string member can be set to 1.2 m. The string member may be a string member that can be cut such that the length of the string member can be adjusted as appropriate according to a situation.

Presence or absence of a hollow does not matter in the string member according to the present invention. The width of the string member may be fixed or not fixed. Examples of the shape of a cross section substantially perpendicular to the longitudinal direction of the string member include shapes same as those in the case of the tubular member. The shape of the cross section may be the same throughout the entire string member or may be different. It is possible to adopt a mode in which a portion (a contact section) that comes into contact with the body duct or the flexible duct in ligation is formed in a tape shape and a section other than the contact section is formed in a thread shape or a mode in which the contact section is formed in a tape shape having width larger than 3 mm and the section other than the contact section is formed in a tape shape having width of 3 mm.

The material of the string member that can be used in the present invention can be selected as appropriate in a range in which the characteristics of the present invention are not spoiled. Examples of the material include plant fiber materials such as cotton, flux, ramie, cannabis, jute, Manila hemp, sisal, maguey, and hemp, animal fiber materials such as silk, wool, gut, mohair, cashmere, camel, llama, alpaca, vicuna, and angora, regenerated fiber such as plant cellulose, and synthetic resin such as nylon, vinylon, polyester, acrylic, polyolefin, polyurethane, and silicone. The material is not limited to a single material and may include two or more materials.

The contact section of the string member in the ligator according to the present invention desirably has a shape and size that do not cause damage to the body duct when the body duct is brought close to the front-end portion of the tubular member and ligated. Such a shape and size of the contact section can be selected as appropriate according to the body duct to be ligated, the material in use, or the like. A tape-like contact section having width (W12) larger than 3 mm is desirable, a tape-like contact section having width of 4 to 10 mm is more desirable, a tape-like contact section having width of 4 to 8 mm is still more desirable, and a tape-like contact section having width of 5 to 7 mm is yet still more desirable.

In the present invention, a scale can be marked in the string member in a range in which the body cavity or the closed spatial body, the body duct, the flexible duct, and the like are not adversely affected. The scale may be marked only in positions before and behind a portion of the string member looped around the body duct or the flexible duct and led out from the back-end portion of the tubular member or may be marked in a portion including the portion, for example, over the entire length of the string member. Examples of a mode for marking the scale include modes same as those of the tubular member.

Examples of the "damage to the body duct" include a tear and breakage of the body duct. Specific examples of the "damage to the body duct" include leakage of lymph due to a tear of a lymph duct, leakage of bile due to a tear of a bile duct, bleeding due to a tear of a blood vessel, and occurrence of thrombus due to breakage of a blood vessel.

The ligator according to the present invention may include a holding instrument inserted through the tubular member, through which the string member is inserted, and capable of holding an end portion of the string member. Such a holding instrument is not specifically limited as long as the holding instrument is inserted through the tubular member, through which the string member is inserted, and is capable of holding the end portion of the string member. Examples of the holding instrument include, besides a gripping forceps used for laparoscopic surgery and the like, a wire-like holding instrument including a hook structure to be pierced through the end portion of the string member or hooked to a ring formed at the end portion of the string member to hold the end portion of the string member and a holding member including a hook-like section formed in a hook shape that can hook one or two string members at a front-end portion thereof and draw the string members into the tubular member. However, the holding member having the hook-like section is desirable.

Figure 5:
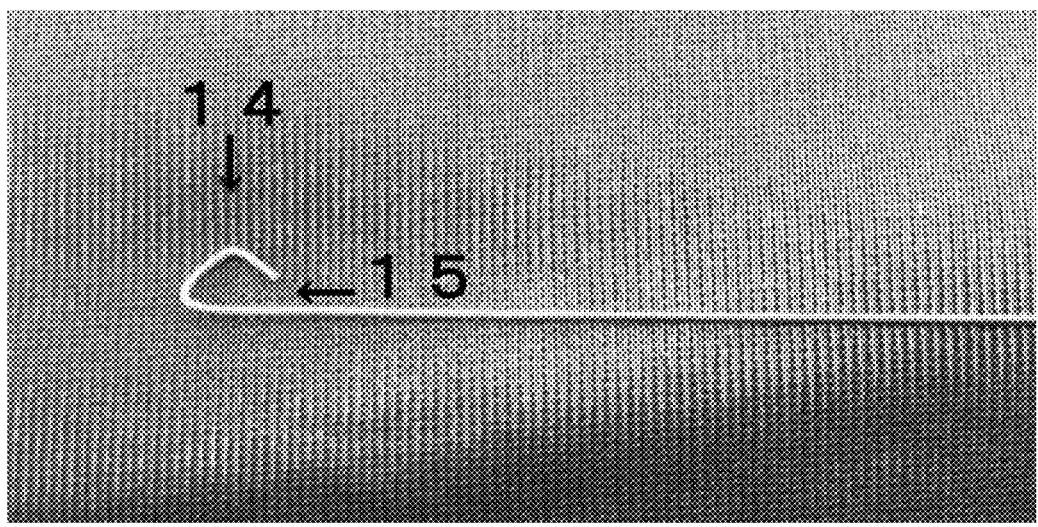
FIG. 5 is a diagram showing a second mode of a front-end portion of a holding instrument 13 according to the embodiment.
Figure 6:
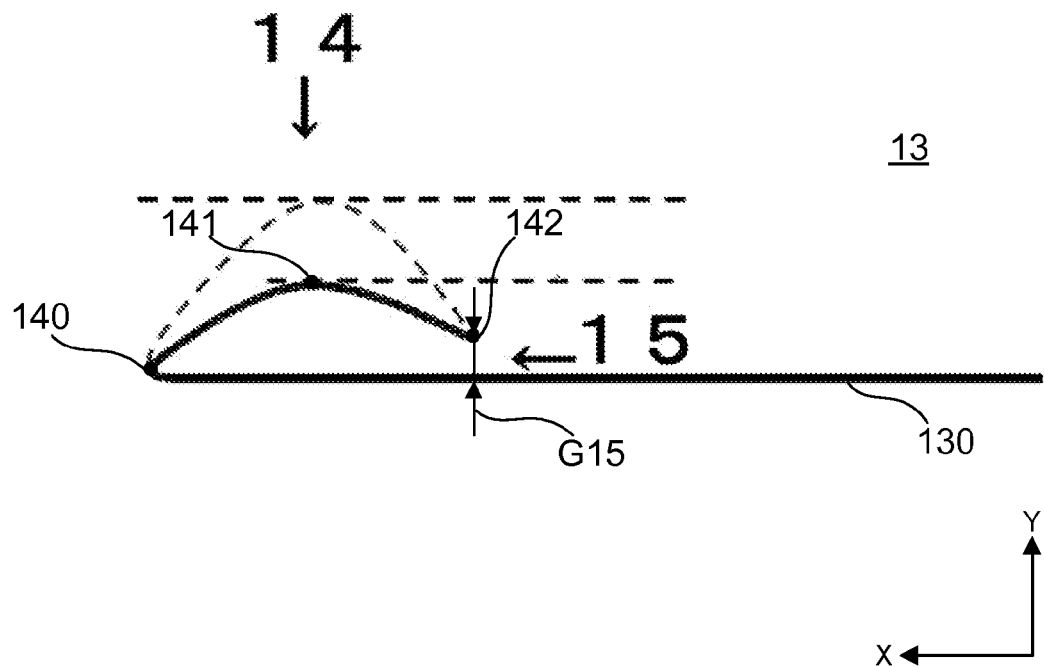
FIG. 6 is a diagram showing a third mode of the front-end portion of the holding instrument 13 according to the embodiment. In the figure, the second mode of the front-end portion of the holding instrument 13 according to the embodiment is indicated by a broken line.
Figure 7:
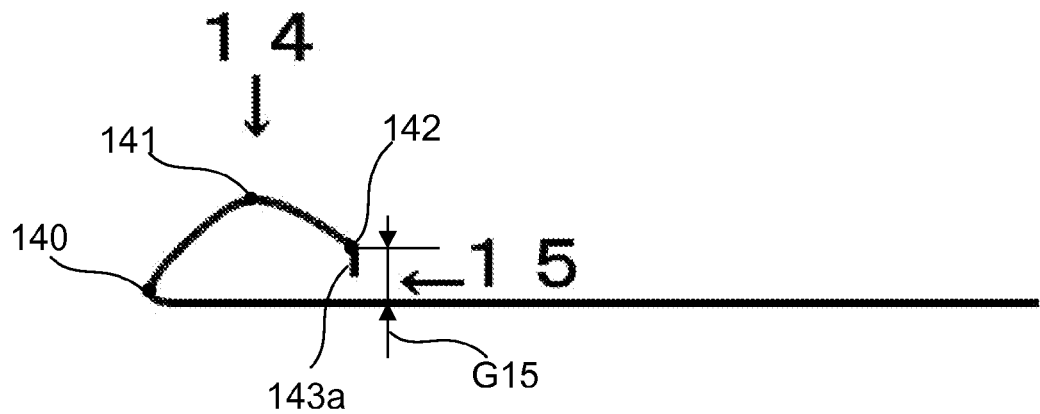
FIG. 7 is a diagram showing a fourth mode of the front-end portion of the holding instrument 13 according to the embodiment.
Figure 8:
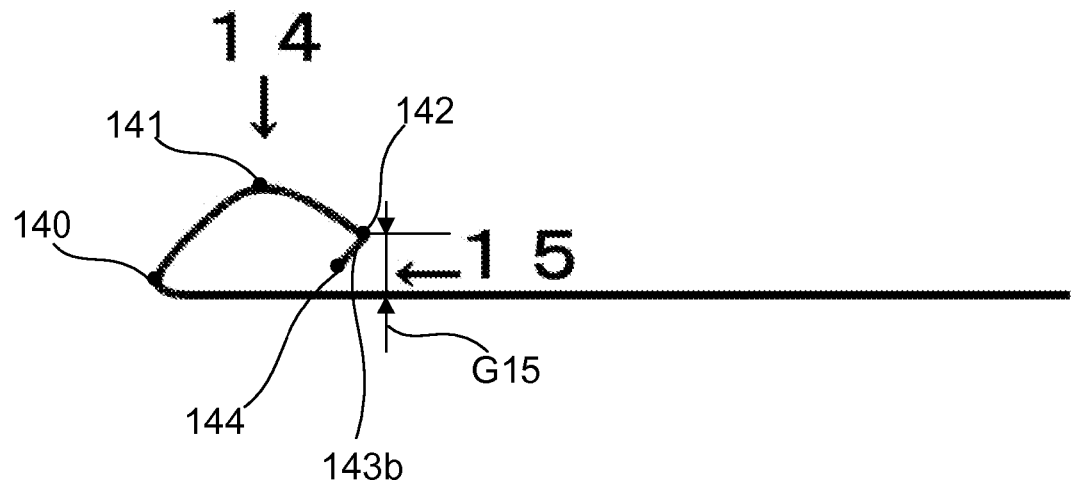
FIG. 8 is a diagram showing a fifth mode of the front-end portion of the holding instrument 13 according to the embodiment.

The hook-like section desirably has a shape for preventing the hooked one or two string members from easily coming off. When holding instrument 13 is configured with rod 130 and the hook-like section, the hook-like section is formed and connected to a leading portion of rod 130. Examples of such a shape include a shape in which the front-end portion of the holding member is bent in a direction substantially perpendicular to the longitudinal direction or an inner direction of the hook-like section. In the embodiments, the hook-like section is in a arch shape and the shape is determined with three points:

i) first one is proximal point 140 that is one end of the hook-like section and is connected to the rod, ii) second one is distal point 142 that is the other end and is the most distant from the leading portion of the rod in the longitudinal direction (X direction) of the rod, iii) third one is vertex point 141 that is located between the proximal point and the distal point and is the most distant from the rod in a vertical direction (Y direction) with respect to the rod. The size (or gap G15) of an opening portion of the hook-like section is desirably size for preventing the opening portion of the hook-like section from being easily caught by the end edge of the tubular member when the hook-like section hooks the string member and draws the string member into the tubular member. Specifically, the size of the opening portion of the hook-like section is more desirably smaller than a difference between the outer diameter and the inner diameter of the tubular member, i.e., thickness δ11 of the tubular member in a range in which the hook-like section can hook one or two string members and draw the string members into the tubular member. Specific examples of the shape of the front-end portion of the holding instrument including the hook-like section according to the present invention include shapes shown in FIGS. 5, 6, 7, 8, and 9. However, the shape of the front-end portion of the holding instrument is not limited to these shapes. Compared with the shape shown in FIG. 5 indicated by a broken line, the shape shown in FIG. 6 is a shape in which the vertex (or vertex point 141) of the hook-like section is low. The shape shown in FIG. 7 is a shape in which the front-end portion of the holding instrument is bent at distal point 142 in the direction (Y direction) substantially perpendicular to the longitudinal direction (X direction). Linear extension 143a lies vertical. The shape shown in FIG. 8 is a shape in which the front-end portion of the holding instrument is bent once at the distal point 142 in the inner direction of the hook-like section. Linear extension 143b inclines toward proximal point 140. The embodiment shown in FIG. 9 has a shape in which the front-end portion of the holding instrument is bent twice (at distal point 142 and at mid point 144) in the inner direction of the hook-like section. Linear portion of extension 143c is determined between mid point 144 and tip point 145, inclining toward vertex point 141.

Figure 2A:
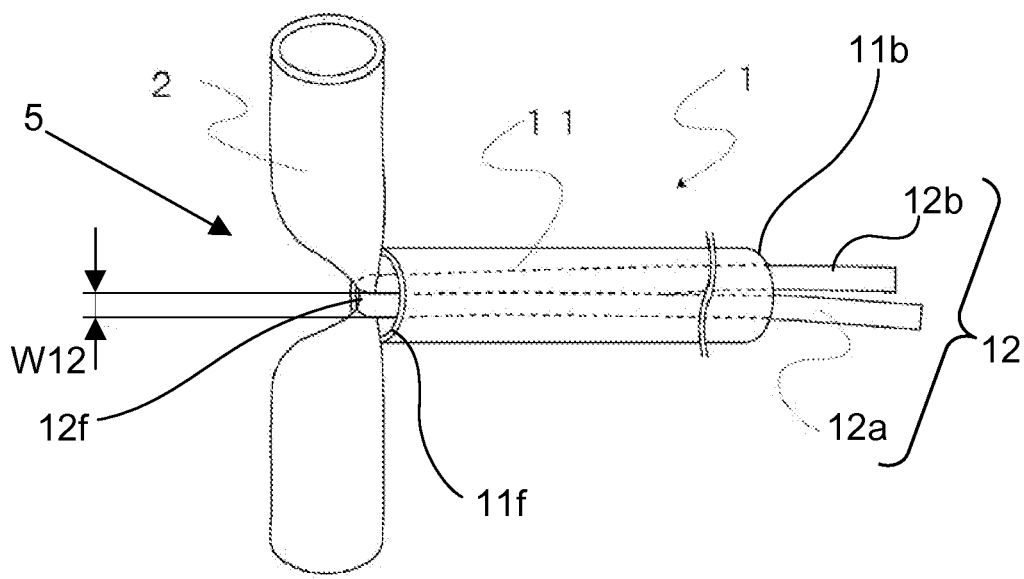
FIGS. 2A and 2B are diagrams showing a mode in which a body duct is brought close to a front-end portion of a tubular member and ligated.
Figure 2B:
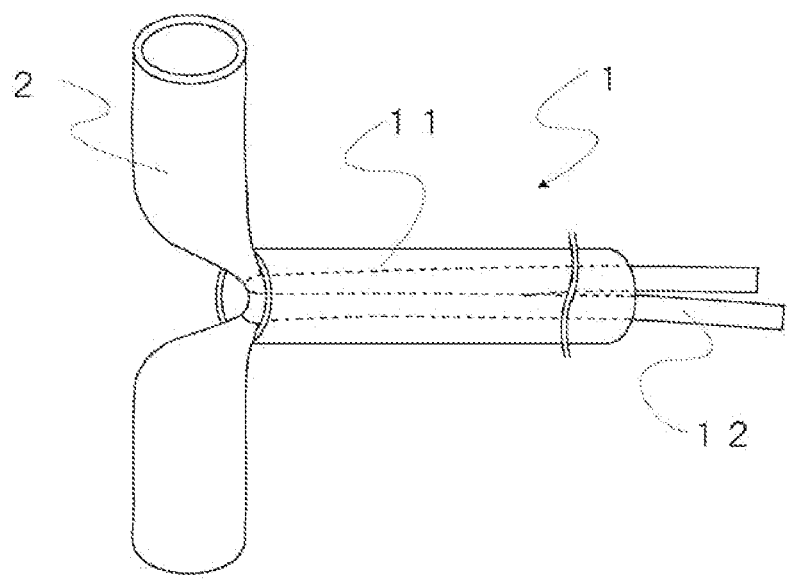
Figure 3A:
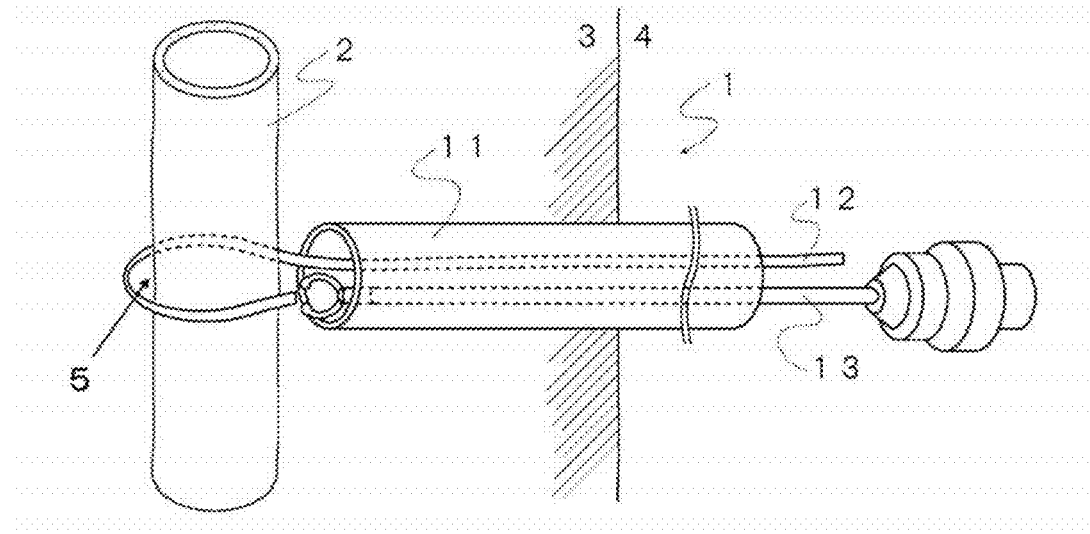
FIGS. 3A and 3B are diagrams showing a second mode of the ligator according to the present invention.
Figure 3B:
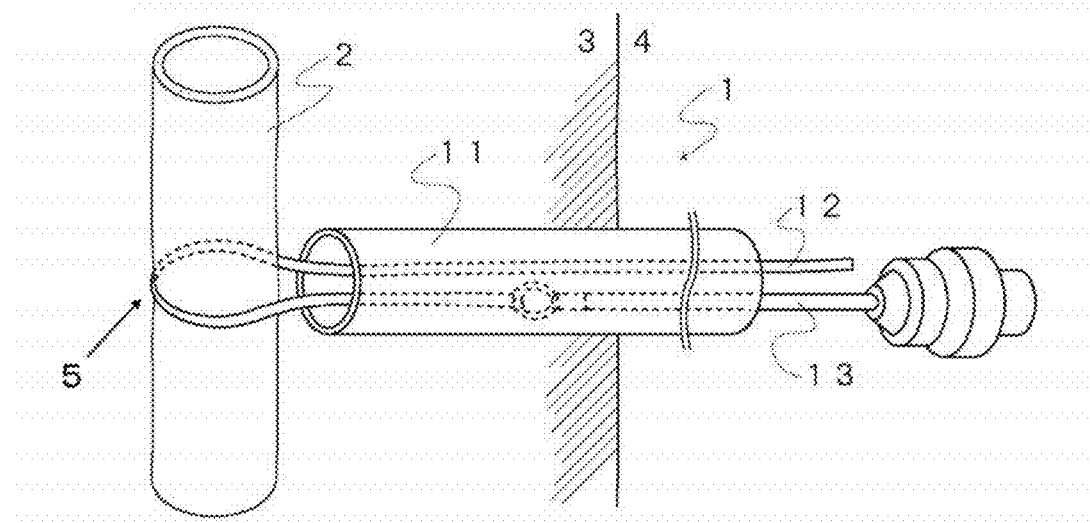
Figure 4:
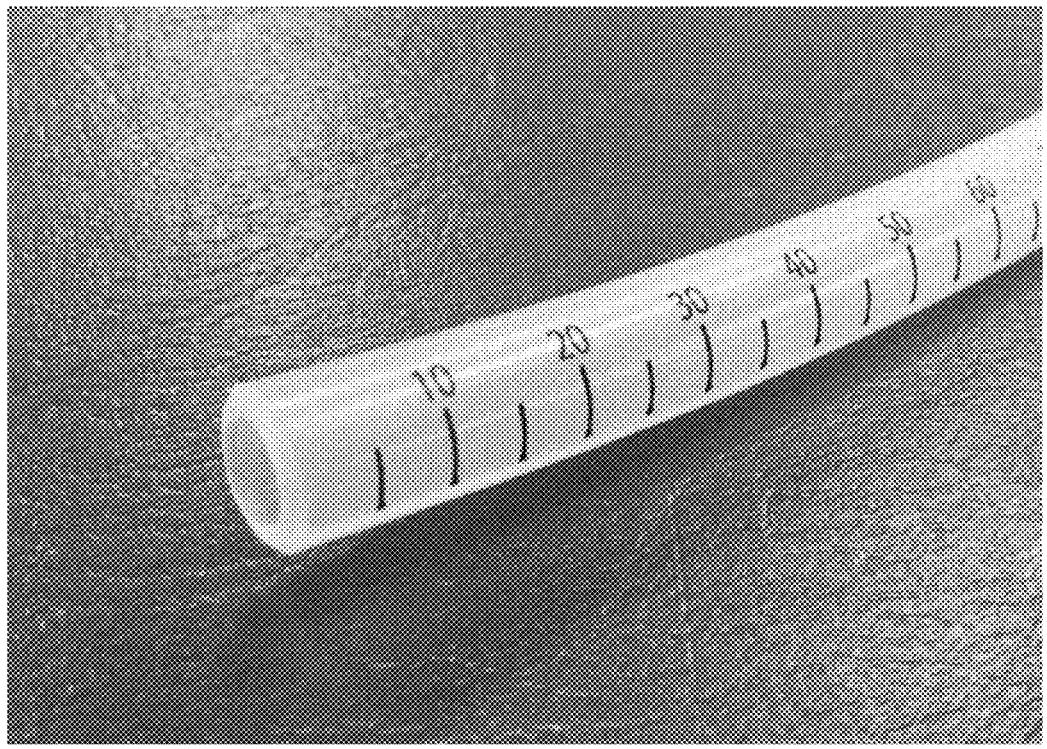
FIG. 4 is a diagram showing a second mode of a front-end portion and an end edge of a tubular member 11 according to an embodiment.
Figure 9:
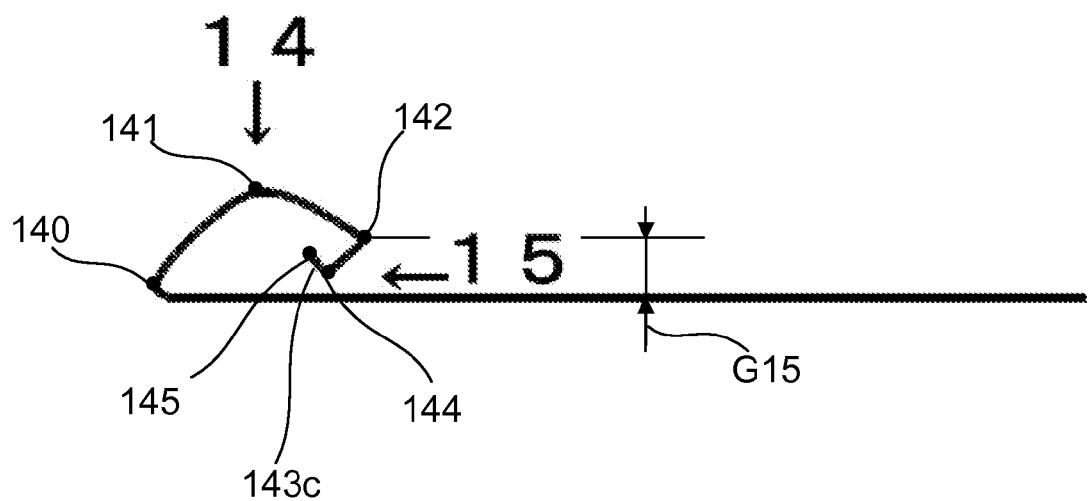
FIG. 9 is a diagram showing a sixth mode of the front-end portion of the holding instrument 13 according to the embodiment.

Next, the action of a ligator 1 according to this embodiment is explained in detail with reference to FIGS. 1, 2A, 2B, 3A, 3B, 4, 5, 6, 7, 8, and 9. FIG. 1 is a diagram showing a first mode of the ligator 1 according to this embodiment. FIGS. 2A and 2B are diagrams showing a mode in which a body duct 2 is brought close to a front-end portion of a tubular member 11 and ligated. FIGS. 3A and 3B are diagrams showing a second mode of the ligator 1 according to this embodiment. FIG. 4 is a diagram showing a second mode of a front-end portion and an end edge of the tubular member 11 according to this embodiment. FIG. 5 is a diagram showing a second mode of a front-end portion of a holding instrument 13 according to this embodiment. FIG. 6 is a diagram showing a third mode of the front-end portion of the holding instrument 13 according to this embodiment. FIG. 7 is a diagram showing a fourth mode of the front-end portion of the holding instrument 13 according to this embodiment. FIG. 8 is a diagram showing a fifth mode of the front-end portion of the holding instrument 13 according to this embodiment. FIG. 9 is a diagram showing a sixth mode of the front-end portion of the holding instrument 13 according to this embodiment.

As shown in FIG. 1, when the body duct 2 is ligated by the ligator 1, first, both end portions of the string member 12 looped around a ligating position 5 of the body duct 2 in a body cavity inside 3 are led out from a back-end portion of the tubular member 11. The front-end portion of the tubular member 11 is arranged in the vicinity of the ligating position 5 of the body duct 2 and the back-end portion of the tubular member 11 is arranged on a body cavity outside 4. A scale indicating distances from the front-end and the back-end is marked in the tubular member 11 as shown in FIG. 4, whereby it is possible to sequentially check or grasp the length of a portion of the tubular member 11 inserted in the body cavity inside 3. Consequently, it is possible to easily arrange the tubular member 11. When the length of the tubular member 11 adjusted by cutting the tubular member 11, it is possible to accurately and easily adjust the length by marking the scale indicating the distances from the front-end and the back-end on the tubular member 11.

Subsequently, in the body cavity outside 4, the body duct 2 is brought close to the front-end portion of the tubular member 11 and ligated by drawing both end portions of the string member 12 (an arrow a) or pushing the tubular member 11 in the front-end direction (an arrow b) or both kinds of operation. Note that scales are marked at least in positions before and behind a portion of the string member 12 looped around the body duct 2 and led out from the back-end portion of the tubular member 11, whereby it is possible to sequentially accurately check a positional relation between the string member 12 and the tubular member 11 when both end portions of the string member 12 are drawn or the tubular member 11 is pushed in the front-end direction or both kinds of operation are performed. Consequently, it is possible to easily grasp how much pressure is applied to the body duct 2 ligated in the ligating position 5.

In the present invention, "looping" the string member 12 "around" the ligating position 5 or the ligation planned region means that the string member 12 is encircled around the ligating position 5 or the ligation planned region or, as shown in FIG. 1, the string member 12 is encircled around the ligating position 5 or the ligation planned region to be folded back.

A mode for bringing the body duct 2 close to the front-end portion of the tubular member 11 and ligating the body duct 2 is different according to, for example, the diameter, flexibility, and elasticity of the body duct 2, the shape of the tubular member 11 and the shape of the cross section substantially perpendicular to the longitudinal direction of the tubular member 11, the outer diameter, the inner diameter, the material, and the structure of the tubular member 11, and the structure, the sectional shape, the thickness, and the material of the contact section of the string member 12. Examples of the mode include a mode in which a loop formed in the vicinity of the front-end portion of the tubular member 11 by the string member 12 looped around the ligating position 5 of the body duct 2 is reduced in size to ligate the body duct 2 as shown in FIG. 2A and a mode in which the body duct 2 is drawn into the tubular member 11 and bent and the inner wall of the body duct 2 comes into contact with an opposed inner wall to ligate the body duct 2 as shown in FIG. 2B. If the end edge of the front-end portion of the tubular member 11 has a shape chamfered as shown in FIG. 4, it is possible to suppress invasion in the ligation of the body duct 2. As shown in FIG. 2A, string member 12 is folded at folding portion 12f. At the portion 12f, the string member is divided into two parts, first string 12a and second string 12b. Folding portion 12f is positioned in the vicinity of front-end portion 11f of tubular member 11 in use. The opposite end of tubular member 11 is denoted with 11b in the drawing.

When the string member 12 looped around the ligating position 5 of the body duct 2 is led out from the back-end portion of the tubular member 11, the holding instrument 13 can be used as shown in FIGS. 3A and 3B. With the holding instrument 13, as shown in FIG. 3A, it is possible to hold the string member 12 inserted through the tubular member 11, through which the string member 12 is inserted, and looped around the ligation planned region of the body duct 2. Further, as shown in FIG. 3B, it is possible to draw the string member 12 into the tubular member 11 and draw out the string member 12 from the back-end portion of the tubular member 11 while keeping the string member 12 held. As a result, it is possible to lead out the front-end portion and the back-end portion of the string member 12 from the back-end portion of the tubular member 11. As shown in FIGS. 5, 6, 7, 8, and 9, when a hook-like section 14 having a hook shape that can hook one or two string members 12 and draw the string members 12 into the tubular member 11 is formed at the front-end portion of the holding instrument 13, after the string member 12 looped around the ligation planned region of the body duct 2 is hooked to an opening portion 15 of the hook-like section 14, it is possible to draw the string member 12 into the tubular member 11 and draw out the string member 12 from the back-end portion of the tubular member 11. When the opening portion 15 of the hook-like section 14 is smaller than the thickness of the tubular member 11, after the string member 12 looped around the ligation planned region of the body duct 2 is hooked, when the string member 12 is drawn into the tubular member 11, the opening portion 15 of the hook-like section 14 is less easily caught by the end edge of the tubular member 11. Therefore, it is possible to easily draw the string member 12 into the tubular member 11. When the front-end portion of the holding instrument 13 is bent in the direction substantially perpendicular to the longitudinal direction as shown in FIG. 7, when the front-end portion of the holding instrument 13 is bent once in the inner direction of the hook-like section 14 as shown in FIG. 8, or when the front-end portion of the holding instrument 13 is bent twice in the inner direction of the hook-like section 14 as shown in FIG. 9, after the string member 12 looped around the ligation planned region of the body duct 2 is hooked to the opening portion 15 of the hook-like section 14, the hooked string member 12 is much less easily comes off. Therefore, it is possible to easily perform operation for drawing the string member 12 into the tubular member 11 and draw out the string member 12 from the back-end portion of the tubular member 11.

Next, the present invention provides a method of ligating a body duct in laparoscopic surgery. A first mode of the method of ligating a body duct in laparoscopic surgery according to the present invention is a method of inserting a front-end portion of a tubular member, into which a string member is inserted and from which a front-end portion of the string member is led out, into a first insertion hole, after looping the front-end portion of the string member around a ligation planned region, inserting the front-end portion of the string member into the tubular member and led out from a back-end portion again to thereby lead out both end portions of the string member from the back-end portion of the tubular member, and, subsequently, ligating the body duct by drawing both end portions of the string member or pushing the tubular member in a front-end direction thereof. That is, the first mode of the method of ligating a body duct in laparoscopic surgery according to the present invention includes the following steps (i) to (v):

(i) a string member front-end portion arranging step for inserting a front-end portion of a tubular member, through which a string member is inserted, into a body cavity from a first insertion hole and arranging, in the vicinity of a ligation planned region of the body duct, a front-end portion of the string member led out from the front-end portion of the tubular member while leaving a back-end portion thereof outside the body cavity;

(ii) a string member looping-around step for inserting a first holding instrument into the body cavity from a second insertion hole, holding the front-end portion of the string member, and looping the string member around the ligation planned region of the body duct;

(iii) a second holding instrument inserting-through step for inserting a second holding instrument from the back-end portion of the tubular member, through which the string member is inserted, and leading out the second holding instrument from the front-end portion of the tubular member;

(iv) a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and (v) a ligating step for ligating the body duct by drawing the drawn-out front-end portion and the back-end portion of the string member and/or pushing the tubular member in a front-end direction thereof.

Next, a second mode of the method of ligating a body duct in laparoscopic surgery according to the present invention is a method of, after inserting a front-end portion of a string member into a first insertion hole and looping the string member around a ligation planned region, leading out the front-end portion of the string member from the first insertion hole, subsequently, inserting the front-end portion and a back-end portion of the string member into a tubular member and inserting a front-end portion of the tubular member into the first insertion hole to thereby lead out both end portions of the string member from a back-end portion of the tubular member, and, subsequently, ligating the body duct by drawing both end portions of the string member or pushing the tubular member in a front-end direction thereof. That is, the second mode of the method of ligating a body duct in laparoscopic surgery according to the present invention includes the following steps (i) to (v):

(i) a string member front-end portion arranging step for holding a front-end portion of a string member with a first holding instrument, inserting the front-end portion of the string member into a body cavity from a first insertion hole, and arranging, in the vicinity of a ligation planned region of the body duct, the front-end portion of the string member while leaving a back-end portion thereof outside the body cavity;

(ii) a string member looping-around step for inserting a second holding instrument into the body cavity from a second insertion hole, holding the front-end portion of the string member, and looping the string member around the ligation planned region of the body duct;

(iii) a string member front-end portion drawing-out step for holding the front-end portion of the looped-around string member with the first holding instrument and drawing out the front-end portion of the string member to the outside of the body cavity from the first insertion hole;

(iv) a tubular member arranging step for inserting, from a front-end portion of a tubular member, both end portions of the string member drawn out to the outside of the body cavity from the first insertion hole, leading out both ends of the string member from a back-end portion of the tubular member, inserting the front-end portion of the tubular member into the body cavity from the first insertion hole, and arranging the front-end portion of the tubular member in the vicinity of the ligation planned region of the body duct while leaving the back-end portion thereof outside the body cavity; and (v) a ligating step for ligating the body duct by drawing both ends of the string member led out from the back-end portion of the tubular member and/or pushing the tubular member in a front-end direction thereof.

Next, a third mode of the method of ligating a body duct in laparoscopic surgery according to the present invention is a method of, after inserting a front-end portion of a string member into a first insertion hole and looping the string member around a ligation planned region, inserting the front-end portion of the string member into a tubular member, a front-end portion of which is inserted into the second insertion hole, leading out the front-end portion of the string member from a back-end portion of the tubular member, and drawing a back-end portion of the string member into a body cavity from the first insertion hole, subsequently, inserting the back-end portion of the string member drawn into the body cavity into the tubular member, the front-end portion of which is inserted into the second insertion hole and leading out the back-end portion of the string member from a back-end portion of the tubular member to thereby lead out both end portions of the string member from the back-end portion of the tubular member, and, subsequently, ligating the body duct by drawing both end portions of the string member or pushing the tubular member in a front-end direction thereof. That is, the third mode of the method of ligating a body duct in laparoscopic surgery according to the present invention includes the following steps (i) to (vi):

(i) a string member front-end portion arranging step for holding a front-end portion of a string member with a first holding instrument, inserting the front-end portion of the string member into a body cavity from a first insertion hole, and arranging the front-end portion of the string member in the vicinity of a ligation planned region of the body duct while leaving a back-end portion thereof outside of the body cavity;

(ii) a string member looping-around step for inserting a front-end portion of a tubular member, through which a second holding instrument is inserted, into the body cavity from a second insertion hole, holding the front-end portion of the string member with the second holding instrument led out from the front-end of the tubular member while leaving a back-end portion thereof outside the body cavity, and looping the string member around the ligation planned region of the body duct;

(iii) a string member front-end portion drawing-out step for drawing the front-end portion of the looped-around string member into the tubular member while keeping the front-end portion held by the second holding instrument, drawing out the front-end portion of the string member from the back-end portion of the tubular member, and drawing the back-end portion of the string member into the body cavity from the first insertion hole;

(iv) a third holding instrument inserting-through step for inserting a third holding instrument from the back-end portion of the tubular member and leading out the third holding instrument from the front-end portion of the tubular member;

(v) a string member back-end portion drawing-out step for holding the back-end portion of the string member with the third holding instrument, drawing the back-end portion of the string member into the tubular member, and drawing out the back-end portion of the string member from the back-end portion of the tubular member; and (vi) a ligating step for ligating the body duct by drawing the drawn-out front-end portion and the back-end portion of the string member and/or pushing the tubular member in a front-end direction thereof.

Next, a fourth mode of the method of ligating a body duct in laparoscopic surgery according to the present invention is a method of, after inserting a front-end portion of a string member into a first insertion hole and looping the string member around a ligation planned region, leading out the front-end portion of the string member from a second insertion hole and drawing a back-end portion of the string member into a body cavity from the first insertion hole, subsequently, leading out the back-end portion of the string member drawn into the body cavity from the second insertion hole, inserting the front-end portion and the back-end portion of the string member into a tubular member, and inserting a front-end portion of the tubular member into the second insertion hole to thereby lead out both end portions of the string member from a back-end portion of the tubular member, and, subsequently, ligating the body duct by drawing both end portions of the string member or pushing the tubular member in a front-end direction thereof. That is, the fourth mode of the method of ligating a body duct in laparoscopic surgery according to the present invention includes the following steps (i) to (vi):

(i) a string member front-end portion arranging step for holding a front-end portion of a string member with a first holding instrument, inserting the front-end portion of the string member into a body cavity from a first insertion hole, and arranging, in the vicinity of a ligation planned region of the body duct, the front-end portion of the string member while leaving a back-end portion thereof outside the body cavity;

(ii) a string member looping-around step for inserting a second holding instrument into the body cavity from a second insertion hole, holding the front-end portion of the string member, and looping the string member around the ligation planned region of the body duct;

(iii) a string member front-end portion drawing-out step for drawing out the front-end portion of the looped-around string member while keeping the front-end portion of the looped-around string member held by the second holding instrument, drawing the back-end portion of the string member into the body cavity from the first insertion hole;

(iv) a string member back-end portion drawing-out step for inserting a third holding instrument into the body cavity from the second insertion hole, holding the back-end portion of the string member, and drawing out the back-end portion of the string member from the second insertion hole;

(v) a tubular member arranging step for inserting, from the front-end portion of the tubular member, the drawn-out front-end portion and the back-end portion of the string member, leading out the front-end portion and the back-end portion of the string member from the back-end portion of the tubular member, inserting the front-end portion of the tubular member into the body cavity from the second insertion hole, and arranging the front-end portion of the tubular member in the vicinity of the ligation planned region of the body duct while leaving the back-end portion thereof outside the body cavity; and (vi) a ligating step for ligating the body duct by drawing the drawn-out front-end portion and the back-end portion of the string member from the back-end portion of the tubular member and/or pushing the tubular member in a front-end direction thereof.

An "insertion hole" in the first to fourth modes of the method of ligating a body duct in laparoscopic surgery according to the present invention refers to a hole-like surgical wound opened in the abdomen of a patient in the laparoscopic surgery. Insertion holes can be formed using a usual method such as a method of inserting a trocar. Forming positions of the insertion holes can be set as appropriate according to the position of a diseased part, the size of an opening, a ligation planned region, operability, and the like. The sizes of the insertion holes can be set as appropriate according to, for example, modes of the tubular member, the first holding instrument, the second holding instrument, the third holding instrument, and the like.

Further, in the first to fourth modes of the method of ligating a body duct in laparoscopic surgery according to the present invention, as the holding instruments, holding instruments same as a holding instrument that can be provided in the ligator according to the present invention can be used. The first holding instrument, the second holding instrument, and the third holding instrument may be the same holding instrument or may be different holding instruments.

The first to fourth modes of the method of ligating a body duct in laparoscopic surgery according to the present invention can be performed more quickly, easily, and without causing damage according to a usual method, for example, by using an endoscope or, for example, filling gas in an abdominal cavity to secure a surgery space in the abdominal cavity. Besides, the first to fourth modes can include any steps in a range in which the characteristics of the present invention are not spoiled.

Next, the present invention provides a method of ligating a body duct. The method of ligating a body duct according to the present invention is a method of arranging a front-end portion of a tubular member, into which a string member is inserted and from which a front-end portion of the string member is led out, in the vicinity of a ligation planned region while leaving a back-end portion of the tubular member outside a body cavity, after looping the front-end portion of the string member around the ligation planned region, inserting the front-end portion of the string member into the tubular member and led out from the back-end portion again to thereby lead out both end portions of the string member from the back-end portion of the tubular member, and, subsequently, ligating the body duct by drawing both end portions of the string member or pushing the tubular member in a front-end direction thereof on the outside of the body cavity. That is, the method of ligating a body duct according to the present invention includes the following steps (i) to (v):

(i) a string member front-end portion arranging step for arranging a front-end portion of a tubular member, through which a string member is inserted, in the vicinity of a ligation planned region of the body duct while leaving a back-end portion thereof outside a body cavity to thereby arrange, in the vicinity of the ligation planned region of the body duct, a front-end portion of the string member led out from the front-end portion of the tubular member;

(ii) a string member looping-around step for holding the front-end portion of the string member with a first holding instrument and looping the string member around the ligation planned region of the body duct;

(iii) a second holding instrument inserting-through step for inserting a second holding instrument from the back-end portion of the tubular member, through which the string member is inserted, and leading out the second holding instrument from the front-end portion of the tubular member;

(iv) a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and (v) a ligating step for ligating the body duct by drawing the drawn-out front-end portion and the back-end portion of the string member and/or pushing the tubular member in a front-end direction thereof.

In the method of ligating a body duct according to the present invention, as the first holding instrument and the second holding instrument, holding instruments same as a holding instrument that can be provided in the ligator according to the present invention can be used. Besides, the first holding instrument may be a hand of a surgeon. When the first holding instrument is not a hand of a surgeon, the first holding instrument and the second holding instrument may be the same holding instrument.

Next, the present invention provides a method of ligating a flexible duct that is present on the inside of a closed spatial body and through which fluid circulates. A first mode of the method of ligating a flexible duct that is present on the inside of a closed spatial body and through which fluid circulates according to the present invention is a method of inserting a front-end portion of a tubular member, into which a string member is inserted and from which a front-end portion of the string member is led out, into a first insertion hole formed in the closed spatial body, and, after looping the front-end portion of the string member around a ligation planned region, inserting the front-end portion of the string member into the tubular member and leading out the front-end portion of the string member from a back-end portion to thereby lead out both end portions of the string member from the back-end portion of the tubular member, and, subsequently, ligating the flexible duct by drawing both end portions of the string member or pushing the tubular member in a front-end direction thereof. That is, the first mode of the method of ligating a flexible duct that is present on the inside of a closed spatial body and through which fluid circulates according to the present invention includes the following steps (i) to (vi):

(i) an insertion hole forming step for forming a first insertion hole communicating with the inside of the closed spatial body and a second insertion hole communicating with the inside of the closed spatial body;

(ii) a string member front-end portion arranging step for inserting a front-end portion of a tubular member, through which a string member is inserted, into the closed spatial body from the first insertion hole and arranging, in the vicinity of a ligation planned region of the flexible duct, through which the fluid circulates, a front-end portion of the string member led out from the front-end portion of the tubular member while leaving a back-end portion thereof outside the closed spatial body;

(iii) a string member looping-around step for inserting a first holding instrument into the closed spatial body from the second insertion hole, holding the front-end portion of the string member, and looping the string member around the ligation planned region of the flexible duct, through which the fluid circulates;

(iv) a second holding instrument inserting-through step for inserting a second holding instrument from the back-end portion of the tubular member, through which the string member is inserted, and leading out the second holding instrument from the front-end portion of the tubular member;

(v) a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and (vi) a ligating step for ligating the flexible duct, through which the fluid circulates, by drawing the drawn-out front-end portion and the back-end portion of the string member and/or pushing the tubular member in a front-end direction thereof.

Next, a second mode of the method of ligating a flexible duct that is present on the inside of a closed spatial body and through which fluid circulates according to the present invention is a method of, after inserting a front-end portion of a string member into a first insertion hole formed in the closed spatial body and looping the string member around a ligation planned region, leading out the front-end portion of the string member from the first insertion hole, subsequently, inserting the front-end portion and a back-end portion of the string member into a tubular member and inserting a front-end portion of the tubular member into the first insertion hole to thereby lead out both end portions of the string member from a back-end portion of the tubular member, and, subsequently, ligating the flexible duct by drawing both end portions of the string member or pushing the tubular member in a front-end direction thereof. That is, the second mode of the method of ligating a flexible duct that is present on the inside of a closed spatial body and through which fluid circulates according to the present invention includes the following steps (i) to (vi):

(i) an insertion hole forming step for forming a first insertion hole communicating with the inside of a closed spatial body and a second insertion hole communicating with the inside of the closed spatial body;

(ii) a string member front-end portion arranging step for holding a front-end portion of a string member with a first holding instrument, inserting the front-end portion of the string member into the closed spatial body from the first insertion hole, and arranging, in the vicinity of a ligation planned region of the flexible duct, through which the fluid circulates, the front-end portion of the string member while leaving a back-end portion thereof outside the closed spatial body;

(iii) a string member looping-around step for inserting a second holding instrument into the closed spatial body from the second insertion hole, holding the front-end portion of the string member, and looping the string member around the ligation planned region of the flexible duct, through which the fluid circulates;

(iv) a string member front-end portion drawing-out step for holding the front-end portion of the looped-around string member with the first holding instrument and drawing out the front-end portion of the string member to the outside of the closed spatial body from the first insertion hole;

(v) a tubular member arranging step for inserting, from a front-end portion of a tubular member, both end portions of the string member drawn out to the outside of the closed spatial body from the first insertion hole, leading out both ends of the string member from a back-end portion of the tubular member, inserting the front-end portion of the tubular member into the closed spatial body from the first insertion hole, and arranging the front-end portion of the tubular member in the vicinity of the ligation planned region of the flexible duct, through which the fluid circulates, while leaving the back-end portion thereof outside the closed spatial body; and (vi) a ligating step for ligating the flexible duct, through which the fluid circulates, by drawing both ends of the string member led out from the back-end portion of the tubular member and/or pushing the tubular member in a front-end direction thereof.

Next, a third mode of the method of ligating a flexible duct that is present on the inside of a closed spatial body and through which fluid circulates according to the present invention is a method of, after inserting a front-end portion of a string member into a first insertion hole formed in a closed spatial body and looping the string member around a ligation planned region, inserting the front-end portion of the string member into a tubular member, a front-end portion of which is inserted into a second insertion hole formed in the closed spatial body, leading out the front-end portion of the string member from a back-end portion of the tubular member, and drawing a back-end portion of the string member into the closed spatial body from the first insertion hole, subsequently, inserting the back-end portion of the string member drawn into the closed spatial body into the tubular member, the front-end portion of which is inserted into the second insertion hole, and leading out the back-end portion of the string member from the back-end portion of the tubular member to thereby lead out both end portions of the string member from the back-end portion of the tubular member, and, subsequently, ligating the flexible duct by drawing both end portions of the string member or pushing the tubular member in a front-end direction thereof. That is, the third mode of the method of ligating a flexible duct that is present on the inside of a closed spatial body and through which fluid circulates according to the present invention includes the following steps (i) to (vii):

(i) an insertion hole forming step for forming a first insertion hole communicating with the inside of the closed spatial body and a second insertion hole communicating with the inside of the closed spatial body;

(ii) a string member front-end portion arranging step for holding a front-end portion of a string member with a first holding instrument, inserting the front-end portion of the string member into the closed spatial body from the first insertion hole, and arranging the front-end portion of the string member in the vicinity of a ligation planned region of the flexible duct, through which the fluid circulates, while leaving a back-end portion thereof outside of the closed spatial body;

(iii) a string member looping-around step for inserting a front-end portion of a tubular member, through which a second holding instrument is inserted, into the closed spatial body from the second insertion hole, holding the front-end portion of the string member with the second holding instrument led out from the front-end of the tubular member while leaving a back-end portion thereof outside the closed spatial body, and looping the string member around the ligation planned region of the flexible duct, through which the fluid circulates;

(iv) a string member front-end portion drawing-out step for drawing the front-end portion of the looped-around string member into the tubular member while keeping the front-end portion held by the second holding instrument, drawing out the front-end portion of the string member from the back-end portion of the tubular member, and drawing the back-end portion of the string member into the closed spatial body from the first insertion hole;

(v) a third holding instrument inserting-through step for inserting a third holding instrument from the back-end portion of the tubular member and leading out the third holding instrument from the front-end portion of the tubular member;

(vi) a string member back-end portion drawing-out step for holding the back-end portion of the string member with the third holding instrument, drawing the back-end portion of the string member into the tubular member, and drawing out the back-end portion of the string member from the back-end portion of the tubular member; and (vii) a ligating step for ligating the flexible duct, through which the fluid circulates, by drawing the drawn-out front-end portion and the back-end portion of the string member and/or pushing the tubular member in a front-end direction thereof.

Next, a fourth mode of the method of ligating a flexible duct that is present on the inside of a closed spatial body and through which fluid circulates according to the present invention is a method of, after inserting a front-end portion of a string member into a first insertion hole formed in a closed spatial body and looping the string member around a ligation planned region, leading out the front-end portion of the string member from a second insertion hole formed in the closed spatial body and drawing a back-end portion of the string member into the closed spatial body from the first insertion hole, subsequently, leading out the back-end portion of the string member drawn into the closed spatial body from the second insertion hole, inserting the front-end portion and the back-end portion of the string member into a tubular member, and inserting a front-end portion of the tubular member into the second insertion hole to thereby lead out both end portions of the string member from a back-end portion of the tubular member, and, subsequently, ligating the flexible duct by drawing both end portions of the string member or pushing the tubular member in a front-end direction thereof. That is, the fourth mode of the method of ligating a flexible duct that is present on the inside of a closed spatial body and through which fluid circulates according to the present invention includes the following steps (i) to (vii):

(i) an insertion hole forming step for forming a first insertion hole communicating with the inside of the closed spatial body and a second insertion hole communicating with the inside of the closed spatial body;

(ii) a string member front-end portion arranging step for holding a front-end portion of a tubular member with a first holding instrument, inserting the front-end portion of the string member into the closed spatial body from the first insertion hole, and arranging, in the vicinity of a ligation planned region of the flexible duct, through which the fluid circulates, the front-end portion of the string member while leaving a back-end portion thereof outside the closed spatial body;

(iii) a string member looping-around step for inserting a second holding instrument into the closed spatial body from the second insertion hole, holding the front-end portion of the string member, and looping the string member around the ligation planned region of the flexible duct, through which the fluid circulates;

(iv) a string member front-end portion drawing-out step for drawing out the front-end portion of the looped-around string member while keeping the front-end portion of the looped-around string member held by the second holding instrument, drawing the back-end portion of the string member into the closed spatial body from the first insertion hole;

(v) a string member back-end portion drawing-out step for inserting a third holding instrument into the closed spatial body from the second insertion hole, holding the back-end portion of the string member, and drawing out the back-end portion of the string member from the second insertion hole;

(vi) a tubular member arranging step for inserting, from the front-end portion of the tubular member, the drawn-out front-end portion and the back-end portion of the string member, leading out the front-end portion and the back-end portion of the string member from the back-end portion of the tubular member, inserting the front-end portion of the tubular member into the closed spatial body from the second insertion hole, and arranging the front-end portion of the tubular member in the vicinity of the ligation planned region of the flexible duct, through which the fluid circulates, while leaving the back-end portion thereof outside the closed spatial body; and (vii) a ligating step for ligating the flexible duct, through which the fluid circulates, by drawing the drawn-out front-end portion and the back-end portion of the string member from the back-end portion of the tubular member and/or pushing the tubular member in a front-end direction thereof.

Next, a fifth mode of the method of ligating a flexible duct that is present on the inside of a closed spatial body and through which fluid circulates according to the present invention is a method of opening the inside of the closed spatial body, arranging a front-end portion of a tubular member, through which a string member is inserted and a front-end portion of the string member is led out, in the vicinity of a ligation planned region while leaving a back-end portion thereof outside the closed spatial body to thereby arrange, and, after looping the front-end portion of the string member around the ligation planned region, inserting the front-end portion of the string member into the tubular member and leading out the front-end portion of the string member from the back-end portion to thereby lead out both end portions of the string member from the back-end portion of the tubular member, and, subsequently, ligating the flexible duct by drawing both end portions of the string member or pushing the tubular member in a front-end direction thereof on the outside of the closed spatial body. That is, the fifth mode of the method of ligating a flexible duct that is present on the inside of a closed spatial body and through which fluid circulates according to the present invention includes the following steps (i) to (vi):

(i) an opening step for opening the inside of the closed spatial body;

(ii) a string member front-end portion arranging step for arranging a front-end portion of a tubular member, through which a string member is inserted, in the vicinity of a ligation planned region of the flexible duct, through which the fluid in the closed spatial body circulates, while leaving a back-end portion thereof outside the closed spatial body to thereby arrange, in the vicinity of the ligation planned region of the flexible duct, through which the fluid in the closed spatial body circulates, a front-end portion of the string member led out from the front-end portion of the tubular member;

(iii) a string member looping-around step for holding the front-end portion of the string member with a first holding instrument and looping the string member around the ligation planned region of the flexible duct, through which the fluid circulates;

(iv) a second holding instrument inserting-through step for inserting a second holding instrument from the back-end portion of the tubular member, through which the string member is inserted, and leading out the second holding instrument from the front-end portion of the tubular member;

(v) a string member front-end portion drawing-out step for holding the front-end portion of the looped-around string member with the second holding instrument, drawing the front-end portion of the string member into the tubular member, and drawing out the front-end portion of the string member from the back-end portion of the tubular member; and (vi) a ligating step for ligating the flexible duct, through which the fluid circulates, by drawing the drawn-out front-end portion and the back-end portion of the string member and/or pushing the tubular member in a front-end direction thereof on the outside of the closed spatial body.

In the first to fourth modes of the method of ligating a flexible duct that is present on the inside of a closed spatial body and through which fluid circulates according to the present invention, the insertion hole is a hole formed in a partition or a barrier in the closed spatial body and refers to a relatively small opening (hole) communicating with the inside of the closed spatial body. The first insertion hole and the second insertion hole in (i) the insertion hole forming step in the present invention can be formed according to a usual method as appropriate to correspond to the structure, the material, the thickness, or the like of the partition or the barrier. The first insertion hole and the second insertion hole can be formed using, for example, a drill, a gimlet, a blade, or the like. However, the first insertion hole and the second insertion hole are not limited to these. Insertion hole forming positions can be set as appropriate according to the sizes of the holes, the ligation planned region, operability, and the like. The sizes of the insertion holes can also be set as appropriate according to, for example, modes of the tubular member, the first holding instrument, the second holding instrument, and the third holding instrument.

Further, the method of ligating a flexible duct that is present on the inside of a closed spatial body and through which fluid circulates according to the present invention can include any steps in a range in which the characteristics of the present invention are not spoiled.

The ligator and the ligation method according to the present invention are explained below on the basis of examples. The technical scope of the present invention is not limited by characteristics indicated by the examples.

EXAMPLES

Example 1

Ligation performed using a blood vessel tape of polyester having width of 3 mm and length of 60 cm and a clamp cover of silicone rubber (VESSEL-CLUDE; Argon Medical Devices, Inc.) having an inner diameter of 5 mm and length of 110 cm, 120 cm, or 130 cm (1) Case 1

The abdomen of a patient A having a tumor in the liver was incised about 10 cm and, after the abdominal incision, using a blood vessel tape of polyester having width of 3 mm and length of 60 cm and a clamp cover of silicone rubber (VESSEL-CLUDE; Argon Medical Devices, Laparoscopy-cm, 120 cm, or 130 cm, the hepatic artery, the portal vein, and the bile duct traveling in the hepatoduodenal ligament were ligated together with the hepatoduodenal ligament to stem the blood. Thereafter, laparoscopy-assisted liver resection was performed according to a usual method to dissect and remove the liver parenchyma in which the tumor was present.

Figure 10:
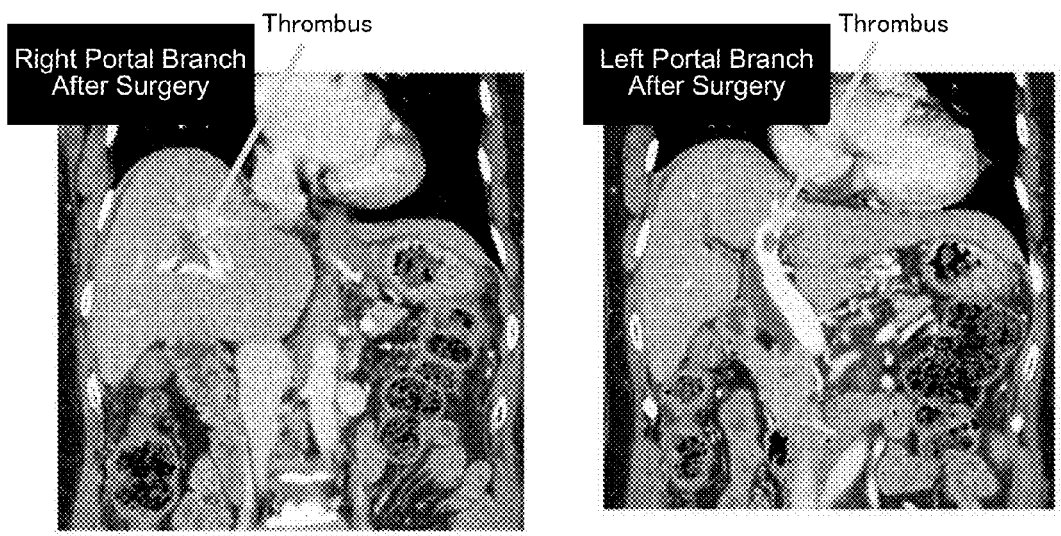
FIG. 10 is diagrams showing CT images in the vertical direction after surgery of a patient A who has undergone laparoscopy-assisted liver resection with blood stemmed using a tape of polyester having width of 3 mm and length of 60 cm and a clamp cover of silicone rubber (VESSEL-CLUDE; Argon Medical Devices, Inc.) having an inner diameter of 5 mm and length of 110 cm, 120 cm, or 130 cm. The left side is a CT image of a position showing a right portal branch and the right side is a CT image of a position showing a left portal branch. In the figure, thrombus that occur in the portal veins are indicated by arrows.

CT images in the vertical direction of the patient A after the surgery are shown in FIG. 10. As shown in FIG. 10, it was confirmed that, although the tumor was removed, thrombus occurred in the right portal branch and the left portal branch.

(2) Case 2

Figure 11:
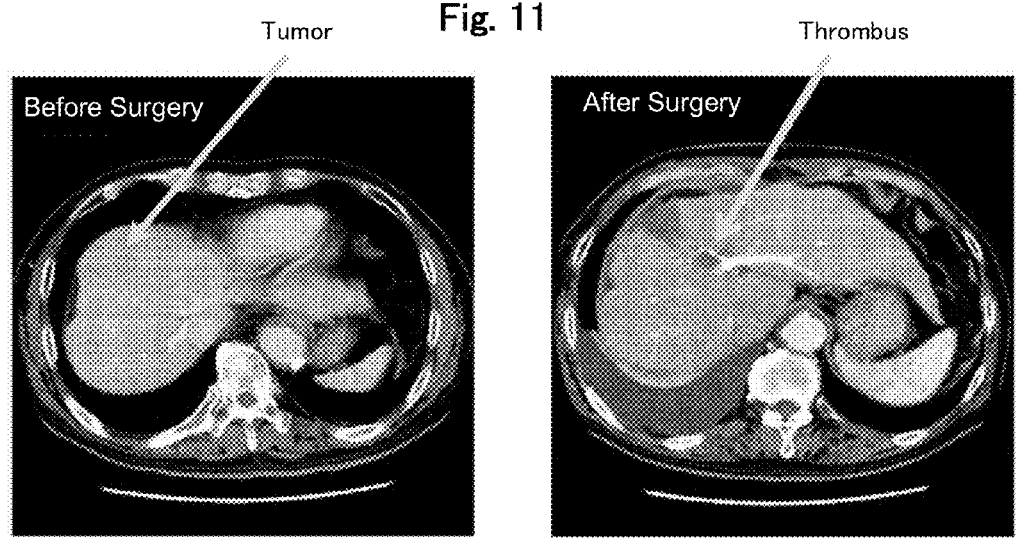
FIG. 11 is diagrams showing CT images in the horizontal direction before and after surgery of a patient B who has undergone laparoscopy-assisted liver resection with blood stemmed using a tape of polyester having width of 3 mm and length of 60 cm and a clamp cover of silicone rubber (VESSEL-CLUDE; Argon Medical Devices, Inc.) having an inner diameter of 5 mm and length of 110 cm, 120 cm, or 130 cm. The left side is a CT image before the surgery. In the figure, a tumor is indicated by an arrow. The right side is a CT image after the surgery. In the figure, thrombus that occurs in a left portal branch is indicated by an arrow.

After stemming the blood according to the method described in the Example (1), laparoscopy-assisted liver resection was performed with a patient B having a tumor in the liver according to a usual method. CT images in the horizontal direction before and after the surgery are shown in FIG. 11. As shown in FIG. 11, it was confirmed that, in the patient B, although the tumor was removed, thrombus occurred in the left portal branch.

From these results, it was clarified that, in some case, thrombus occurs in the portal vein when the hepatoduodenal ligament is ligated using the blood vessel tape of polyester having width of 3 mm and the clamp cover of silicone rubber having an inner diameter of 5 mm.

Example 2

Ligation performed using a tape of polyester having width of 5 mm and length of 1 m and a tube of silicone rubber having an outer diameter of 10 mm, an inner diameter of 5 to 6 mm and length of 30 cm A tape of polyester having width of 5 mm and length of 1 m inserted through a tube of silicone rubber having an outer diameter of 10 mm, an inner diameter of 5 to 6 mm and length of 30 cm was prepared and used as a ligator. Six trocars in total having a diameter of 12 mm were inserted into the abdomen of a patient C having an 8 cm tumor in the posterior segment of the right lobe. The prepared ligator was inserted into one of the trocars. The hepatic artery, the portal vein, and the bile duct traveling in the hepatoduodenal ligament were ligated together with the hepatoduodenal ligament to stem the blood using the ligator. Thereafter, pure laparoscopic liver resection was performed according to a usual method to dissect and remove the liver parenchyma in which the tumor was present.

Figure 12:
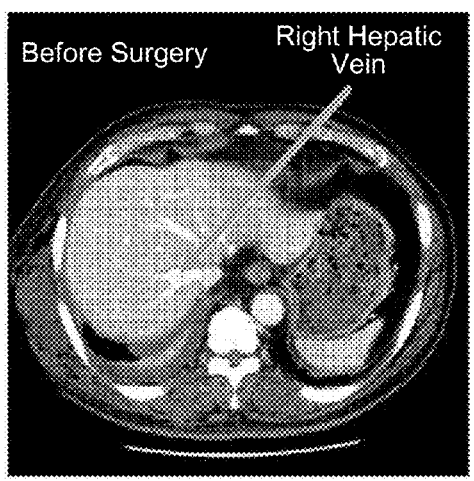
FIG. 12 is diagrams showing CT images in the horizontal direction before and after surgery of a patient C who has undergone pure laparoscopic liver resection with blood stemmed using a tape of polyester having width of 5 mm and length of 1 m and a tube of silicone rubber having an outer diameter of 10 mm, an inner diameter of 5 to 6 mm and length of 30 cm. The upper diagram is a CT image before the surgery and the lower diagram is a CT image after the surgery. In the right diagrams, "same regions" indicated by arrows respectively indicate the same positions as the right hepatic veins indicated by arrows in the left diagrams. In the upper right diagram, a tumor is indicated by an arrow. In the lower diagrams, regions of the excised tumor are indicated by arrows.
Figure 12:
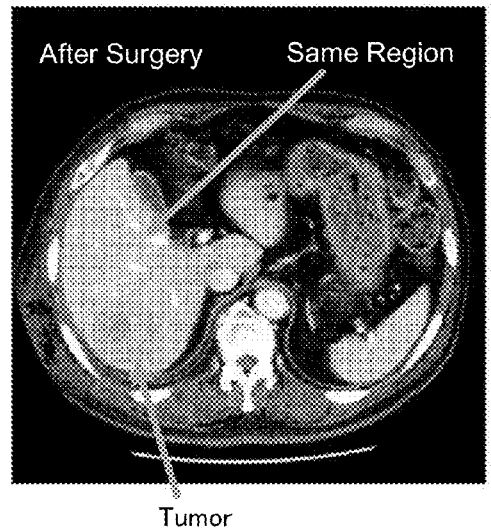
Figure 12:
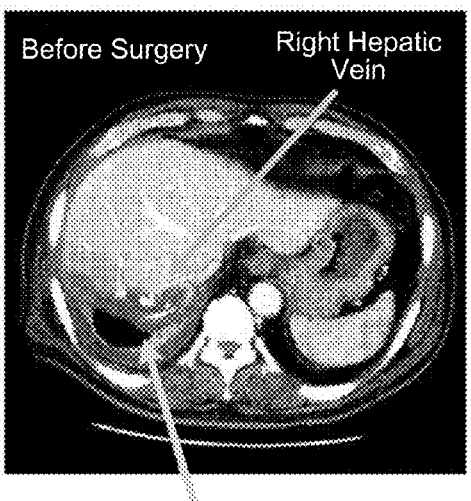
Figure 12:
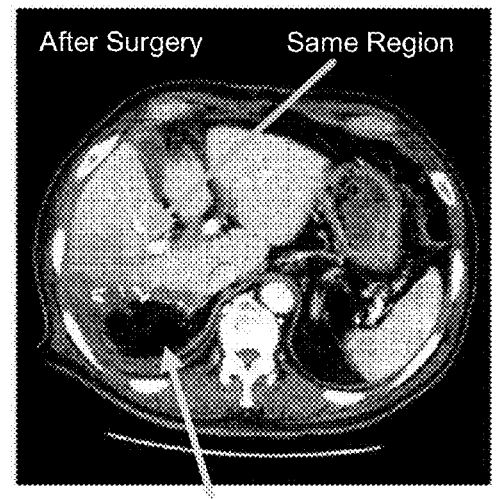

CT images in the horizontal direction before and after the surgery are shown in FIG. 12. As shown in FIG. 12, it was confirmed that, in the patient C, the tumor was completely excised. Occurrence of bleeding during the surgery and thrombus after the surgery was not observed.

From these results, it was clarified that it is possible to extremely effectively and safely perform hemostasis in pure laparoscopic liver resection by ligating, together with the hepatoduodenal ligament, the hepatic artery, the portal vein, and the bile duct traveling in the hepatoduodenal ligament using the tape of polyester having width of 5 mm and length of 1 m and the tube of silicone rubber having an outer diameter of 10 mm, an inner diameter of 5 to 6 mm and length of 30 cm. Further, it was clarified that it is possible to safely excise, in pure laparoscopic surgery, a relatively large tumor present in the posterior segment, which is considered difficult to be excised in the pure laparoscopic surgery in the past, by performing hemostasis using the tape and the tube.

Note that the examples explained above are applied to not only a method of ligating a body duct but also a method of ligating a flexible duct that is present on the inside of a closed spatial body and through which fluid circulates.

REFERENCE SIGNS LIST 1 ligator
2 body duct
3 body cavity inside 4 body cavity outside
5 ligating position
11 tubular member
12 string member
13 holding instrument
14 hook-like section
15 opening portion

The invention claimed is:

1. A ligator for ligating one or more body ducts in a body cavity, the ligator comprising:
    a tubular member and a string member for bringing the body ducts close to a front-end portion of the tubular member, the string member being folded at a folding portion defining a first string and a second string of the string member, wherein
    the tubular member has an inner diameter allowing the first string and the second string of the string member to be inserted therethrough and has length extending from a ligating position of the body ducts in the body cavity to an outside of the body cavity,
    the string member has length equal to or larger than a double of the length extending from the ligating position to the outside of the body cavity, and
    the folding portion of the string member is in a tape form and has a width that is ranged from 3 mm to 7 mm, and
    a holding instrument that is configured with a rod and a hook-like section, the rod being linear and the hook-like section being in an arch shape and connected to the rod at a leading portion of the rod, wherein
    the arch shape is defined with three points,
        first one being a proximal point that is one end and is connected to the rod,
        second one being a distal point that is the other end and is the most distant from the leading portion of the rod in a longitudinal direction with respect to the rod, and
        third one being a vertex point that is located between the proximal point and the distal point in the longitudinal direction and that is more distant from the rod in a vertical direction, which is perpendicular to the longitudinal direction, than the distal point,
    an opening portion is formed between the distal point and the rod with a gap,
    the gap is smaller than a thickness of the tubular member, the thickness being defined by a half difference between inner and outer diameters of the tubular member,
    the distal portion futher includes an extension that is liner extending from the distal point, the extension being formed by folding the hook-like section one time at the distal point, and
    the extension substantially lies in the vertical direction with respect to the rod.

2. The ligator according to claim 1, wherein the string member has a shape and size for preventing a contact section that comes into contact with the body ducts from causing damage to the body ducts when the body ducts are brought close to the front-end portion of the tubular member and ligated.

3. The ligator according to claim 1, wherein the string member has scales marked in positions before and behind a portion where the string member is looped around the body ducts and led out from a back-end portion of the tubular member.

4. The ligator according to claim 1, wherein the tubular member is a tubular member that is not bent by a pressing force received in a longitudinal direction thereof or is not reduced in length in the longitudinal direction.

5. The ligator according to claim 1, wherein the tubular member has marked thereon a scale indicating distances from a front-end and/or a back-end thereof.

6. The ligator according to claim 5, wherein
    the tubular member is made of a material that is soft enough to be cut with a cutting tool including a knife and a pair of scissors.

7. The ligator according to claim 1, wherein the tubular member is chamfered at end edges of a front-end and/or a back-end thereof.

8. The ligator according to claim 1, further comprising a holding instrument that can hold an end portion of the string member while being inserted through the tubular member, through which the string member is inserted.

9. The ligator according to claim 8, wherein the holding instrument includes, at a front-end portion thereof, a hook-like section formed in a hook shape capable of catching a singularity of or a pair of the string members and drawing the string members into the tubular member.

10. The ligator according to claim 1, wherein
    a color of the tubular member is different from a color of the string member or the body duct.

11. The ligator according to claim 1, wherein
    a color of the tubular member is different from a color of a flexible duct that is present on an inside of a closed spatial body and through which fluid circulates.

12. The ligator according to claim 1, wherein
    an outer diameter of the tubular member is smaller than an opening that is a surgical wound created on a patient so that the tubular member is capable to be inserted through the opening.

13. The ligator according to claim 12, wherein
    the outer diameter of the tubular member is more than 5 mm and equal to or less than 10 mm.

14. A ligator for ligating one or more body ducts in a body cavity, the ligator comprising:
    a tubular member and a string member for bringing the body ducts close to a front-end portion of the tubular member, the string member being folded at a folding portion defining a first string and a second string of the string member, wherein
    the tubular member has an inner diameter allowing the first string and the second string of the string member to be inserted therethrough and has length extending from a ligating position of the body ducts in the body cavity to an outside of the body cavity,
    the string member has length equal to or larger than a double of the length extending from the ligating position to the outside of the body cavity, and
    the folding portion of the string member is in a tape form and has a width that is ranged from 3 mm to 7 mm, and
    a holding instrument that is configured with a rod and a hook-like section, the rod being linear and the hook-like section being in an arch shape and connected to the rod at a leading portion of the rod, wherein
    the arch shape is defined with three points,
        first one being a proximal point that is one end and is connected to the rod,
        second one being a distal point that is the other end and is the most distant from the leading portion of the rod in a longitudinal direction with respect to the rod, and
        third one being a vertex point that is located between the proximal point and the distal point in the longitudinal direction and that is more distant from the rod in a vertical direction, which is perpendicular to the longitudinal direction, than the distal point, an opening portion is formed between the distal point and the rod with a gap, the gap is smaller then a thickness of the tubular member, the thickness being defined by a half difference between inner and outer diameters of the member, the distal portion further includes an extension that is linear extending from the distal point, the extension being formed by the folding the hook-like section one time at the distal point, and the extension inclines toward the proximal point.

15. A ligator for ligating one or more body ducts in a body cavity, the ligator comprising:

a tubular member and a string member for bringing the body ducts close to the front-end portion of the tubular member, the string member being folded at a folding portion defining a first string and a second string of the string member, wherein the tubular member has an inner diameter allowing the first string and the second string of the string member to be inserted therethrough and has length extending from a ligating position of the body ducts in the body cavity to an outside of the body cavity, the string member has length equal to or larger than a double of the length extending from the ligating position to the outside of the body cavity, and the folding portion of the string member is in a tape form and has a width that is ranged from 3 mm to 7 mm, and a holing instrument that is configured with a rod and a hook-like section, the rod being linear and the hook-like section being in an arch shape and connected to the rod at a leading portion of the rod, wherein the arch shape is defined with three points, first one being a proximal point that is one end and is connected to the rod, second one being a distal point that is the other end and is the most distant from the leading portion of the rod in a longitudinal direction with respect to the rod, and third one being a vertex point that is located between the proximal point and the distal point in the longitudinal direction and that is more distant from the rod in a vertical direction, which is perpendicular to the longitudinal direction, than the distal point, an opening portion is formed between the distal point and the rod with a gap, the gap is smaller than a thickness of the tubular member, the thickness being defined by a half difference between inner and outer diameters of the tubular member, the distal portion further includes an extension that extends from the distal point, the extension being formed by folding the hook-like section two times at the distal point and a mid point, a linear portion being formed between the mid point and a tip point of the extension, the linear portion inclines toward the vertex point of the hook-like section.

\* \* \* \* \*